United States Patent
Kagaya et al.

(10) Patent No.: US 9,826,891 B2
(45) Date of Patent: Nov. 28, 2017

(54) ENDOSCOPE APPARATUS AND IMAGE PICKUP CONTROL METHOD THEREOF

(71) Applicant: FUJIFILM Corporation, Tokyo (JP)

(72) Inventors: Makoto Kagaya, Ashigarakami-gun (JP); Masayuki Takahira, Ashigarakami-gun (JP); Shingo Masuno, Ashigarakami-gun (JP); Masanobu Uchihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 262 days.

(21) Appl. No.: 14/104,539

(22) Filed: Dec. 12, 2013

(65) Prior Publication Data
US 2014/0171737 A1 Jun. 19, 2014

(30) Foreign Application Priority Data
Dec. 14, 2012 (JP) ................. 2012-274003

(51) Int. Cl.
*A61B 1/04* (2006.01)
*A61B 1/12* (2006.01)
(Continued)

(52) U.S. Cl.
CPC .......... *A61B 1/051* (2013.01); *A61B 1/00006* (2013.01); *A61B 1/00009* (2013.01);
(Continued)

(58) Field of Classification Search
CPC . A61B 1/00006; A61B 1/00009; A61B 1/015; A61B 1/045; H04N 5/2327;
(Continued)

(56) References Cited

U.S. PATENT DOCUMENTS 4,175,545 A    11/1979    Termanini
5,817,015 A * 10/1998    Adair ................. A61B 1/00101
                                                                     600/121
(Continued)

FOREIGN PATENT DOCUMENTS

EP          0025958 A2    4/1981
EP          2557774 A1    2/2013
(Continued)

OTHER PUBLICATIONS

European Office Comminucation and Extended European Search Report dated Jun. 3, 2014, issued in European Application No. 13197095.6.
(Continued)

*Primary Examiner* — Timothy J Neal
*Assistant Examiner* — Aaron B Fairchild
(74) *Attorney, Agent, or Firm* — Birch, Stewart, Kolasch & Birch, LLP

(57) ABSTRACT

An endoscope apparatus including: an image pickup device; a detection device that detects whether or not an image region at which a part of an object region is edged along a direction parallel to the scan lines in a state that is different to a case where a plurality of the scan lines are simultaneously exposed exists in a frame image due to differences of exposure timings for each of the scan lines of the image pickup device based on an image feature amount in the frame image that is obtained from the image data for each of the scan lines that is outputted from the image pickup device; and an exposure control device that changes an exposure time of each of the scan lines by the image pickup device simultaneously for all of the scan lines if the detection device detects the image region.

11 Claims, 32 Drawing Sheets

(51) Int. Cl.
*H04N 5/335* (2011.01)
*A61B 1/05* (2006.01)
*H04N 5/232* (2006.01)
*H04N 5/235* (2006.01)
*H04N 5/353* (2011.01)
*A61B 1/00* (2006.01)
*A61B 1/015* (2006.01)
*A61B 1/045* (2006.01)
*G06T 7/13* (2017.01)
*G06T 7/174* (2017.01)

(52) U.S. Cl.
CPC .............. *A61B 1/015* (2013.01); *A61B 1/045* (2013.01); *G06T 7/13* (2017.01); *G06T 7/174* (2017.01); *H04N 5/2327* (2013.01); *H04N 5/2353* (2013.01); *H04N 5/23277* (2013.01); *H04N 5/3532* (2013.01); *G06T 2207/10016* (2013.01); *G06T 2207/10068* (2013.01); *G06T 2207/30004* (2013.01)

(58) Field of Classification Search
CPC .... H04N 5/2353; H04N 5/351; H04N 5/3532; H04N 5/35536; H04N 5/35554; H04N 5/3535; H04N 5/23277
USPC ................. 600/109, 117, 118, 160; 348/296
See application file for complete search history.

(56) References Cited

U.S. PATENT DOCUMENTS

| | | | |
|---|---|---|---|
| 2005/0093996 A1* | 5/2005 | Kinoshita | H04N 5/2357 348/226.1 |
| 2009/0213212 A1 | 8/2009 | Nakamura | |
| 2010/0069713 A1* | 3/2010 | Endo | A61B 1/0005 600/109 |

FOREIGN PATENT DOCUMENTS

| | | |
|---|---|---|
| JP | 2009-201540 A | 9/2009 |
| JP | 2011-206336 A | 10/2011 |
| JP | 2012-143319 A | 8/2012 |

OTHER PUBLICATIONS

European Office Communication and Extended European Search Report dated Jun. 3, 2014, issued in European Application No. 13197093.1.

Office Action dated Feb. 8, 2016 for co-pending U.S. Appl. No. 14/104,559.

* cited by examiner

FIG.11
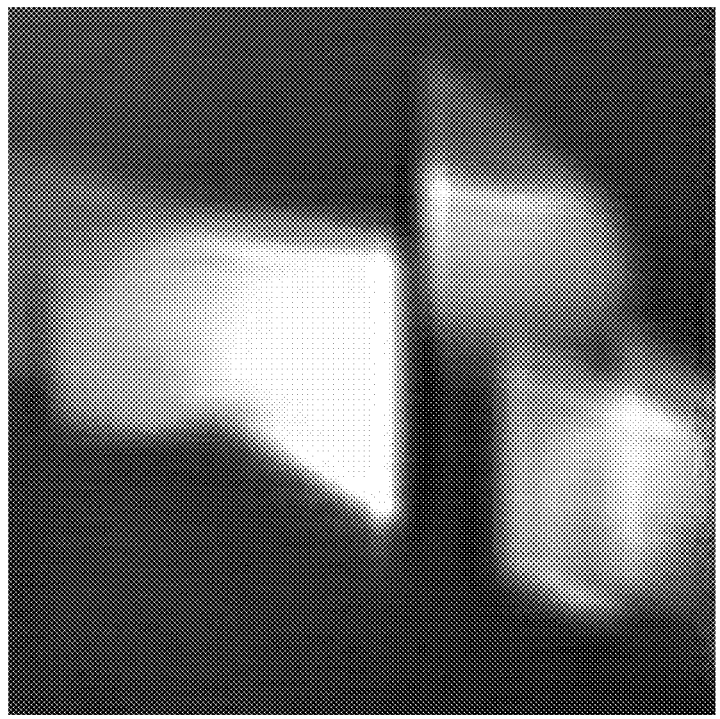
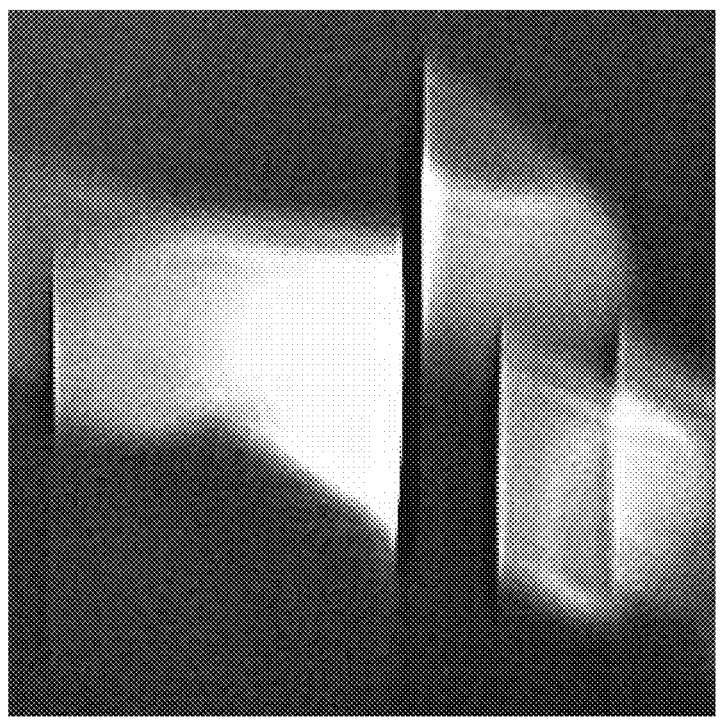

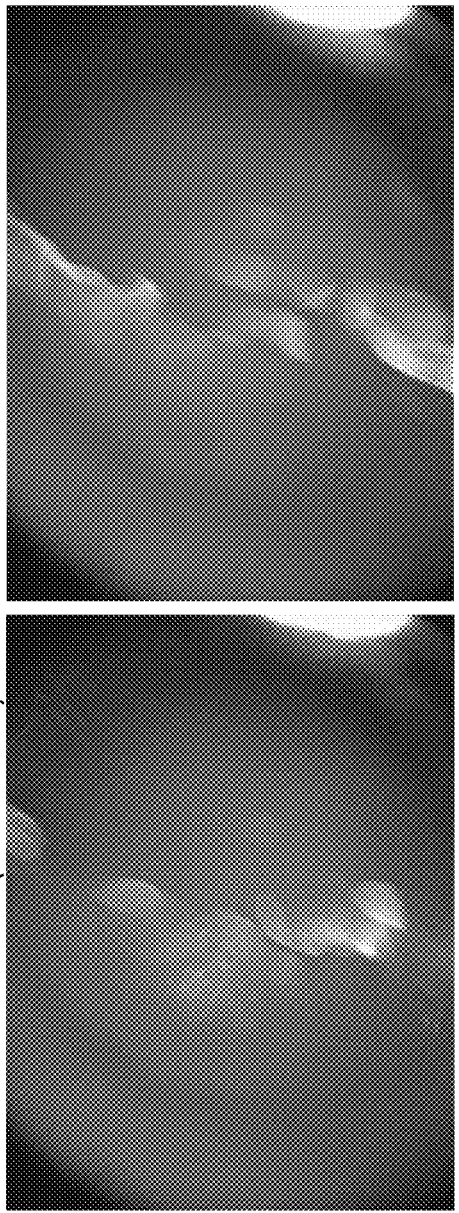
FIG.22A (PSEUDO) GLOBAL SHUTTER
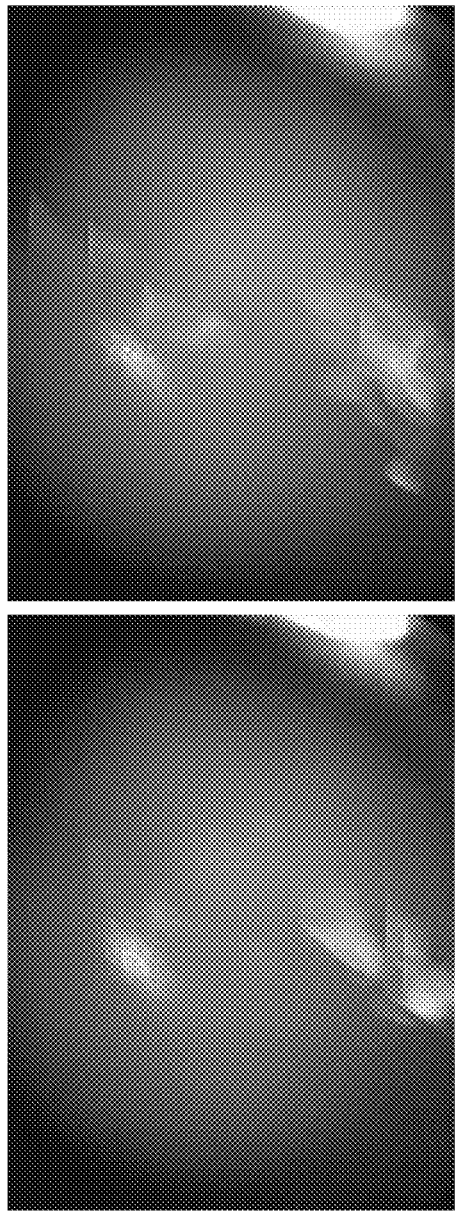
FIG.22B ROLLING SHUTTER

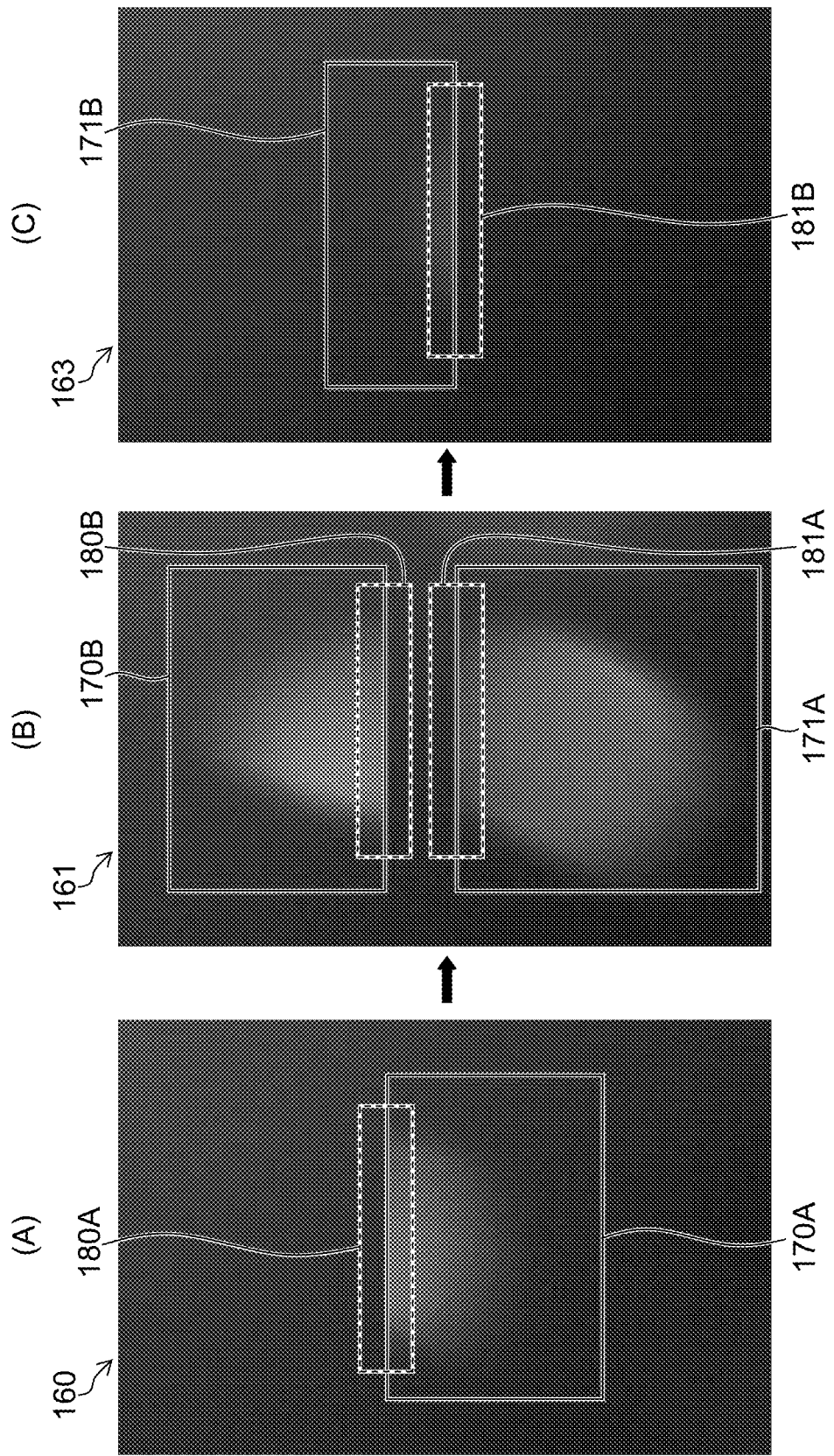

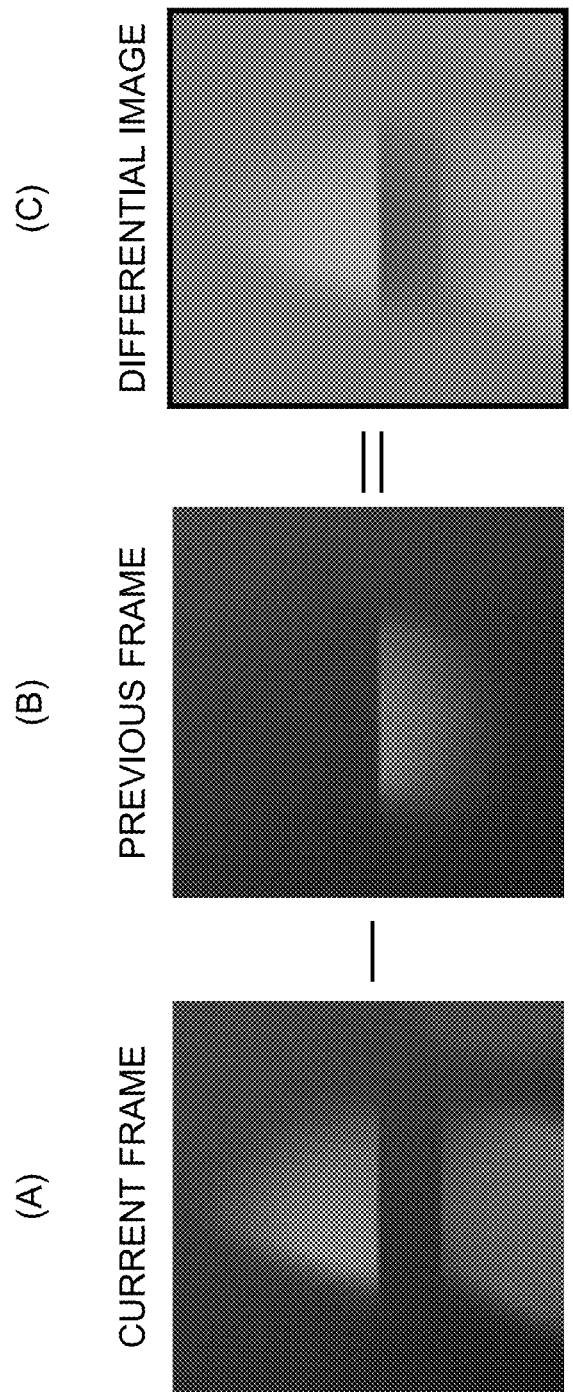

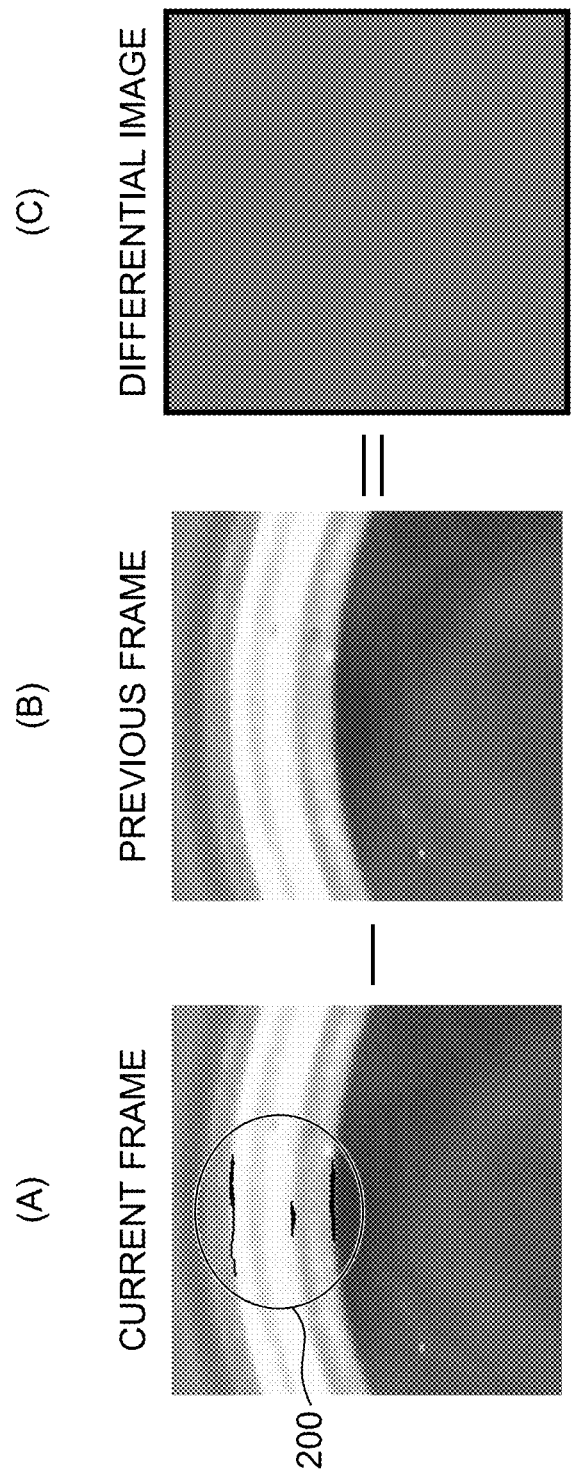

ENDOSCOPE APPARATUS AND IMAGE PICKUP CONTROL METHOD THEREOF

BACKGROUND OF THE INVENTION

Field of the Invention

The present invention relates to an endoscope apparatus and an image pickup control method thereof, and more particularly to an endoscope apparatus having a CMOS type solid-state image pickup element in a distal end portion of an endoscope, and an image pickup control method of the endoscope apparatus.

Description of the Related Art

Medical diagnosis utilizing an endoscope system is actively performed in the medical field. An endoscope system includes: an electronic endoscope that has an insertion portion that is inserted into a body cavity; a processor apparatus to which the electronic endoscope is detachably connected, and which receives an image pickup signal that is outputted from a solid-state image pickup element built into the electronic endoscope and performs image processing thereon, and outputs an observation image to a monitor; and a light source apparatus that generates light that passes through a light guide inside the electronic endoscope and illuminates the inside of the body cavity.

Although conventionally CCD (a charge coupled device) type image pickup elements have been generally used as solid-state image pickup elements that are mounted in electronic endoscopes, in recent years CMOS (a complementary metal oxide semiconductor) type solid-state image pickup elements which enable low-voltage driving and with which demands for larger numbers of pixels and high-speed reading are easily met are also being used.

Further, in the case of utilizing a CMOS type solid-state image pickup element, a CMOS process can be used in the manufacturing process, and peripheral circuits such as a drive circuit or a processing circuit can be combined within the same chip, which is also useful for miniaturization.

For the aforementioned reasons, various kinds of electronic endoscopes equipped with a CMOS type solid-state image pickup element have been proposed in recent years (for example, see Japanese Patent Application Laid-Open No. 2012-143319, Japanese Patent Application Laid-Open No. 2011-206336, and Japanese Patent Application Laid-Open No. 2009-201540).

Generally, in most CMOS type solid-state image pickup elements a plurality of pixels are disposed in a matrix shape on a light receiving surface (image pickup surface), and exposure control by a rolling shutter method is performed. The rolling shutter method is a method that performs an exposure operation for each scan line in a sequential manner, in which resetting is performed in sequence for each scan line and storing of charges is started, and read out of the stored charges is then performed sequentially.

SUMMARY OF THE INVENTION

In an electronic endoscope in which a CMOS type solid-state image pickup element that is driven by a rolling shutter method is mounted, when spraying air or water from an air/water feeding nozzle provided in an endoscope distal end portion, if a droplet that is scattered when performing suction of body fluid from a forceps outlet or the like appears in a video of the electronic endoscope, a phenomenon has been confirmed that a linear unnatural edge arises along a horizontal direction in an image of the droplet (reflected light from the droplet). In the present specification, the aforementioned phenomenon is referred to as an "edging phenomenon".

Since the aforementioned edging phenomenon is a phenomenon that is not observed in an electronic endoscope in which a CCD image pickup element is mounted, it is a phenomenon that many users are unfamiliar with. Further, since the edging phenomenon randomly occurs while droplets are scattering, it may also appear as block-shaped noise.

Accordingly, it is desirable to eliminate this in order not to arise misunderstandings such that the phenomenon is due to a failure or low performance.

The present invention has been conceived in view of the above described circumstances, and an object of the present invention is to provide an endoscope apparatus that can prevent an edging phenomenon that an unnatural edge arises in a droplet image that appears in an observation video of an endoscope from being visually recognized by an observer, and an image pickup control method of the endoscope apparatus.

To achieve the above described object, one aspect of an endoscope apparatus of the present invention includes: an image pickup device in which a plurality of pixels are arranged in a matrix shape, and which starts sequential exposure by at least one of scan lines with respect to the plurality of pixels to generate image data, and outputs image data for each of the scan lines in an order of starting exposure; a detection device that detects whether or not an image region at which a part of an object region is edged along a direction parallel to the scan lines in a state that is different to a case where a plurality of the scan lines are simultaneously exposed exists in a frame image due to differences of exposure timings for each of the scan lines of the image pickup device based on an image feature amount in the frame image that is obtained from the image data for each of the scan lines that is outputted from the image pickup device; and an exposure control device that changes an exposure time of each of the scan lines by the image pickup device simultaneously for all of the scan lines if the detection device detects the image region.

Another aspect of the endoscope apparatus of the present invention includes: an image pickup device in which a plurality of pixels are arranged in a matrix shape, and which starts sequential exposure by at least one of scan lines with respect to the plurality of pixels to generate image data, and outputs image data for each of the scan lines in an order of starting exposure; a fluid operation detection device that detects a fluid operation that performs feeding or suction of a fluid to or from inside of a body; and an exposure control device that changes an exposure time of each of the scan lines by the image pickup device simultaneously for all of the scan lines if the fluid operation detection device detects the fluid operation.

Further, to achieve the above described object, one aspect of an image pickup control method of an endoscope apparatus according to the present invention includes: a step of starting sequential exposure by at least one of scan lines with respect to a plurality of pixels that are arranged in a matrix shape to generate image data, and outputting image data for each of the scan lines in an order of starting exposure; a step of detecting whether or not an image region at which a part of an object region is edged along a direction parallel to the scan lines in a state that is different to a case where a plurality of the scan lines are simultaneously exposed exists in a frame image due to differences of exposure timings for each of the scan lines based on an image feature amount in the frame image that is obtained from the image data for each of the scan lines; and a step of changing an exposure time of each of the scan lines simultaneously for all of the scan lines if the image region is detected.

Further, another aspect of the image pickup control method of the endoscope apparatus of the present invention includes: a step of starting sequential exposure by at least one of scan lines with respect to a plurality of pixels that are arranged in a matrix shape to generate image data, and outputting image data for each of the scan lines in an order of starting exposure; a step of detecting a fluid operation that performs feeding or suction of a fluid to or from inside of a body; and a step of changing an exposure time of each scan line simultaneously for all of the scan lines if the fluid operation is detected.

According to the present invention, it is possible to prevent an edging phenomenon in which an unnatural edge arises in a droplet image that appears in an observation video of an endoscope from being visually recognized by an observer.

BRIEF DESCRIPTION OF THE DRAWINGS

FIG. 11 is an explanatory drawing used to describe edging phenomenon mitigation processing of form (a);

FIGS. 13A and 13B are views that focus on and illustrate the timing of an exposure period (charge storage period) of each line of the image pickup element with respect to only two frames that are temporally adjacent, in which FIG. 13A is a view illustrating a case in which an exposure time is 1/200 sec, and FIG. 13B is a view illustrating a case in which an exposure time is 1/60 sec;

FIGS. 22A and 22B are views that compare a droplet image when the image pickup element was driven using the pseudo-global shutter method, and a droplet image when the pickup element is driven using the rolling shutter method at a time of normal imaging;

FIG. 23 is an explanatory drawing used to describe edging phenomenon detection processing of form (1);

FIG. 30 is an explanatory drawing used to describe erroneous detection prevention processing of form (X-1);

FIG. 31 is an explanatory drawing used to describe the erroneous detection prevention processing of form (X-1);

DETAILED DESCRIPTION OF THE PREFERRED EMBODIMENTS

Preferred embodiments of the present invention are described in detail hereunder in accordance with the accompanying drawings.

Figure 1:
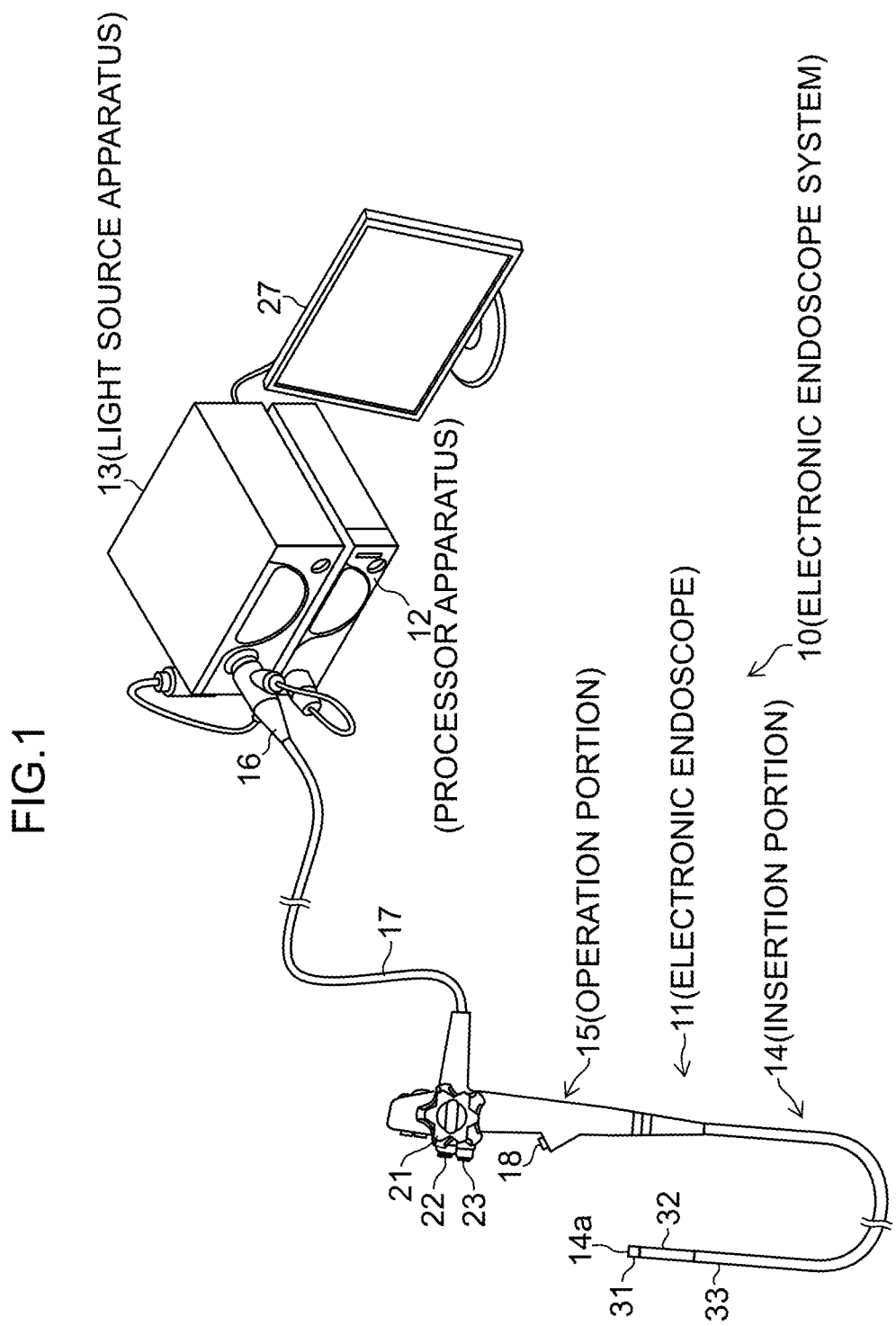
FIG. 1 is a configuration diagram illustrating the overall configuration of an electronic endoscope system to which the present invention is applied.

In FIG. 1, an electronic endoscope system 10 includes an electronic endoscope 11 (hereunder, referred to as "endoscope 11"), a processor apparatus 12, and a light source apparatus 13.

The electronic endoscope 11 has a flexible insertion portion 14 that is inserted into a subject (patient), an operation portion 15 that is connected to a proximal end portion of the insertion portion 14, a connector 16 that is connected to the processor apparatus 12 and the light source apparatus 13, and a universal cord 17 that connects the operation portion 15 and the connector 16.

A forceps port 18 is provided on a distal end side of the operation portion 15. A treatment instrument such as an electric knife is inserted through the forceps port 18. The forceps port 18 communicates through a forceps channel inside the insertion portion 14 with a forceps outlet 20 at a distal end face 14a of the insertion portion 14 that is shown in FIG. 2.

The operation portion 15 includes various operation members such as an angle knob 21, an air/water feeding button 22, a suction button 23, and a release button. The angle knob 21 causes a distal end rigid portion 31 of the insertion portion 14 to bend in the upward, downward, left, and right directions when subjected to a rotary operation. The air/water feeding button 22 causes air or water to be sprayed from an air/water feeding nozzle 43 provided in the distal end face 14a as shown in FIG. 2 when subjected to a pressing operation. When the suction button 23 is subjected to a pressing operation, substances to be sucked such as body fluid and tissue inside the body are sucked from the forceps outlet 20 shown in FIG. 2.

The processor apparatus 12 is electrically connected to the endoscope 11 and the light source apparatus 13, and performs overall control of the operations of the electronic endoscope system 10.

Figure 2:
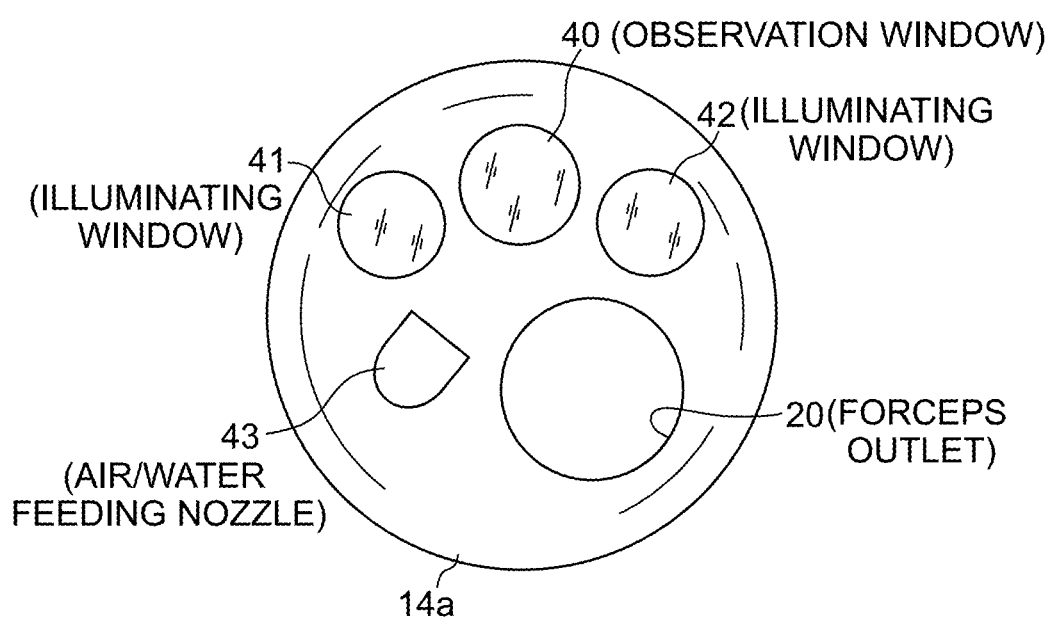
FIG. 2 is a front view that illustrates a distal end face of an endoscope insertion portion.

As shown in FIG. 2, an image pickup unit (image pickup apparatus) that performs imaging through an observation window 40 provided in the distal end face 14a is mounted in the distal end rigid portion 31. Electric power and control signals from the processor apparatus 12 are supplied to the image pickup unit via the universal cord 17 and a signal cable that is inserted through the insertion portion 14, so that the operations of the image pickup unit are controlled by the processor apparatus 12.

Image pickup signals from the image pickup unit are supplied to the processor apparatus 12 via the signal cable. Various kinds of processing are performed on the image pickup signals at the processor apparatus 12 to generate image data of an observation image that is being observed by the image pickup unit.

A monitor 27 is connected to the processor apparatus 12. An observation image that is being imaged by the image pickup unit is displayed on a screen of the monitor 27 based on image data from the processor apparatus 12.

As an illumination device that emits illuminating light at an object with respect to which the image pickup unit picks up an image, the light source apparatus 13 supplies illuminating light to the endoscope 11 that is to be emitted towards a site to be observed from illuminating windows 41 and 42 provided in the distal end face 14a, as shown in FIG. 2. The illuminating light supplied from the light source apparatus 13 is transmitted to the distal end rigid portion 31 via the universal cord 17 and a light guide that is inserted through the insertion portion 14.

Figure 3:
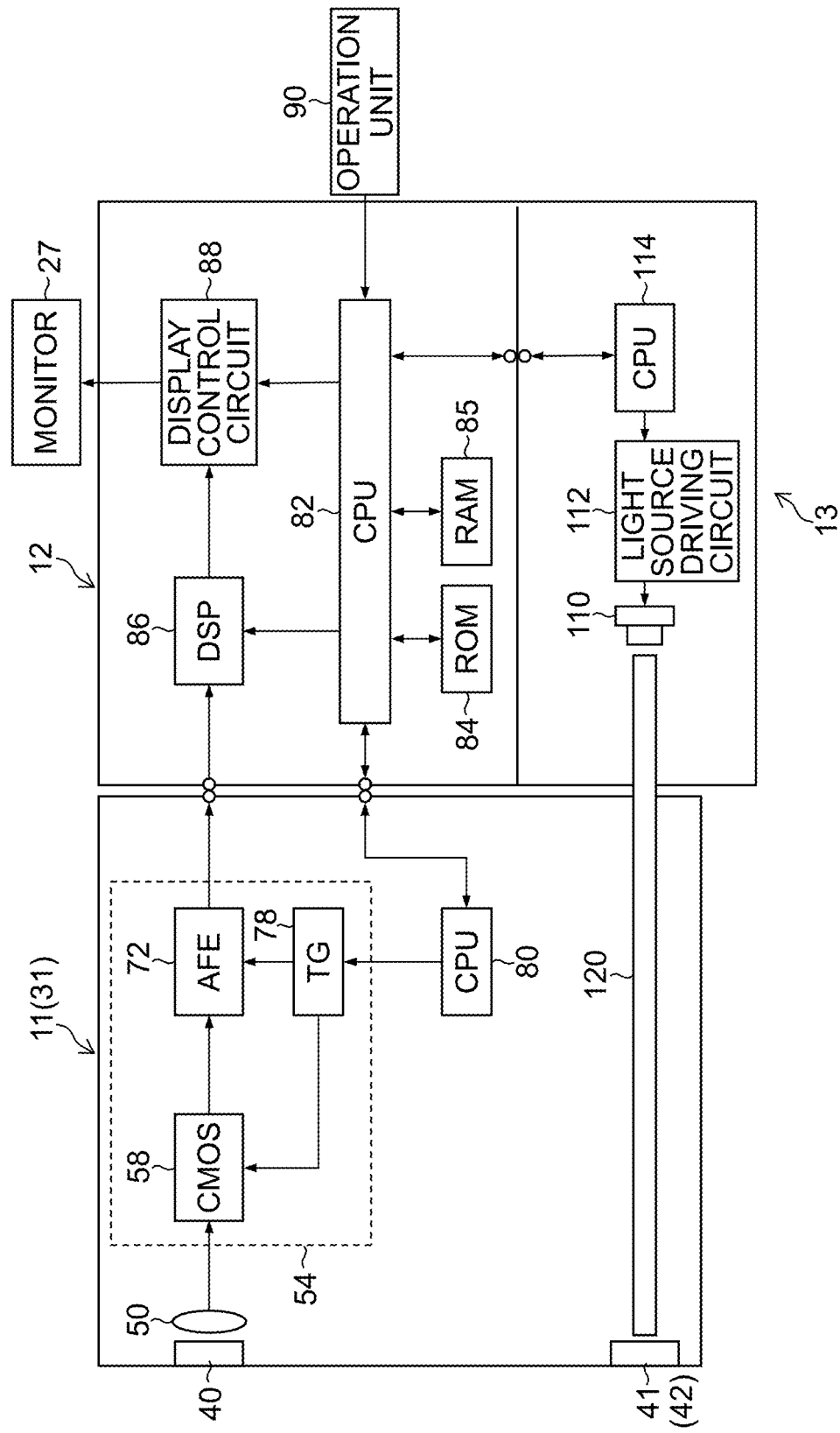
FIG. 3 is a configuration diagram that illustrates the configuration of a control system of the electronic endoscope system to which the present invention is applied.

FIG. 3 is a configuration diagram that illustrates the configuration of a control system of the endoscope system 10. As shown in FIG. 3, as an image pickup unit (image pickup apparatus) 54, an MOS type (CMOS) image pickup element 58 (hereunder, referred to simply as "image pickup element 58"), an analog signal processing circuit (AFE: analog front end) 72, a TG (timing generator) 78 and the like are provided in the distal end rigid portion 31 of the endoscope 11. The distal end rigid portion 31 is also equipped with a CPU 80.

Based on control by the CPU 80, the TG 78 generates drive pulses (vertical/horizontal scanning pulses, reset pulses and the like) for the image pickup element 58 and a synchronization pulse for the AFE 72. The image pickup element 58 that is an image pickup device is driven by a drive pulse inputted from the TG 78 and subjects an optical image that is formed on an image pickup surface via the observation window 40 of the distal end face 14a and an objective optical system 50 to photoelectric conversion and outputs the resulting signal as an image pickup signal.

A large number of pixels are disposed in a matrix shape on the image pickup surface of the image pickup element 58, and a photosensor (photoelectric conversion element) is provided in each pixel. Light that is incident on the image pickup surface of the image pickup element 58 is stored as a charge in the photosensor of each pixel. Subsequently, by performing scanning in the vertical direction and the horizontal direction by means of a vertical scanning circuit and a horizontal scanning circuit (neither of which is shown in the drawings), signal charge amounts stored in the photosensors of the respective pixels are read out sequentially as pixel signals and outputted at a predetermined frame rate.

Note that, although omitted from the drawings, the image pickup element 58 is a single-plate color solid-state image pickup element equipped with color filters (for example, primary color filters in a Bayer array) formed by a plurality of color segments.

The configuration of a signal read-out circuit that reads out the stored charges of the respective photosensors of the image pickup element 58 as image pickup signals is known, and a common configuration such as, for example, a three transistor configuration or a four transistor configuration thereto. Descriptions thereof will be omitted herein.

The AFE 72 includes a correlated double sampling (CDS) circuit, an automatic gain circuit (AGC), and an analog-to-digital converter. The CDS circuit performs correlated double sampling processing on an image pickup signal that is outputted from the image pickup element 58, and removes reset noise and amplitude noise that arises at the image pickup element 58.

The AGC amplifies an image pickup signal from which noise has been removed by the CDS circuit, by a gain (amplification factor) that is specified by the CPU 80. The analog-to-digital converter converts the image pickup signal that was amplified by the AGC to a digital signal of a predetermined number of bits and outputs the resulting signal.

The image pickup signal that was converted to a digital signal and outputted by the AFE 72 (digital image pickup signal) is inputted to the processor apparatus 12 through a signal wire.

Note that circuits for driving the image pickup element 58 and the configuration inside the distal end rigid portion 31 for sending an image pickup signal from the image pickup element 58 to the processor apparatus 12 are not limited to the above described circuits and configuration.

The processor apparatus 12 includes the CPU 82, a ROM 84, a RAM 85, an image processing circuit (DSP) 86, and a display control circuit 88.

The CPU 82 controls each portion within the processor apparatus 12 and also performs overall control of the entire electronic endoscope system 10. Various programs for controlling the operations of the processor apparatus 12 as well as data used for control are stored in the ROM 84. Programs executed by the CPU 82 and data and the like is temporarily stored in the RAM 85.

Based on control performed by the CPU 82, the DSP 86 performs color interpolation, color separation, a color balance adjustment, a gamma adjustment, image enhancement processing and the like with respect to the image pickup signal inputted from the AFE 72 and generates image data.

Image data that is outputted from the DSP 86 is inputted to the display control circuit 88. The display control circuit 88 converts the image data inputted from the DSP 86 into a signal format corresponding to the monitor 27 and causes the image data to be displayed on the screen of the monitor 27.

Various buttons that can accept the input of an instruction from a user are provided on an operation unit 90 of the processor apparatus 12.

The light source apparatus 13 is configured to include a light source 110, a light source driving circuit 112, and a CPU 114. The CPU 114 performs communication with the CPU 82 of the processor apparatus 12, and performs control of the light source driving circuit 112.

The light source 110 is, for example, a xenon lamp, and is controlled so as to turn on or off by the light source driving circuit 112. Illuminating light emitted by the light source 110 is introduced to an incident end of a light guide 120 that is constructed by bundling multiple optical fibers. The illuminating light that is transmitted through the light guide 120 is emitted from an exit end of the light guide 120 and irradiated onto a site to be observed through the illuminating windows 41 and 42 of the endoscope 11.

When observing the inside of a body cavity using the endoscope system 10 configured as described above, the power sources of the endoscope 11, the processor apparatus 12, the light source apparatus 13, and the monitor 27 are turned on, the insertion portion 14 of the endoscope 11 is inserted into the body cavity, and an image of the inside of the body cavity that is picked up by the image pickup element 58 of the image pickup unit 54 is observed using the monitor 27 while illuminating the inside of the body cavity with illuminating light from the light source apparatus 13.

The method of driving the image pickup element 58 when imaging a dynamic image of an object by means of the image pickup unit 54 will now be described.

Figure 4:
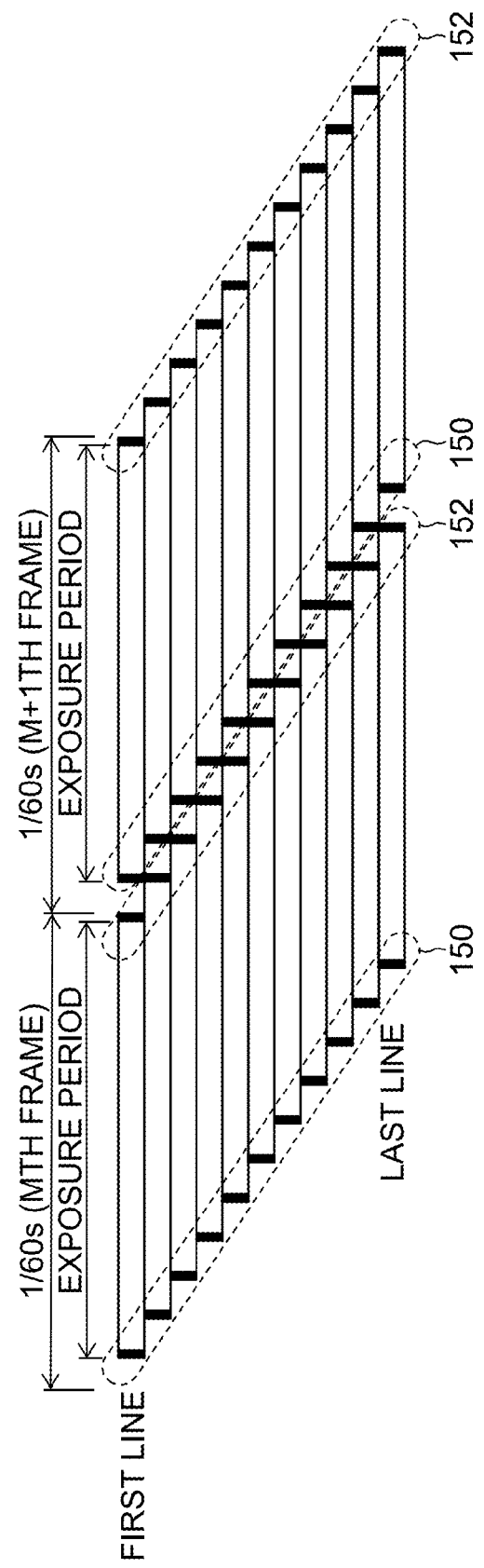
FIG. 4 is a view that focuses on and illustrates the timing of an exposure period (charge storage period) of each pixel row (line) of an image pickup element with respect to only two frames (an Mth frame and an M+1th frame) that are temporally adjacent.

FIG. 4 is a view that focuses on and illustrates a timing (exposure timing) of an exposure period (charge storage period) of each pixel row, that is, each scan line (hereunder, referred to as "line"), of the image pickup element 58 with respect to only two temporally adjacent frames (an Mth frame and an M+1th frame). Note that, to simplify the drawing, the illustrated number of lines is different to the actual number of lines.

As shown in FIG. 4, fundamentally the image pickup element 58 is driven by a known rolling shutter method. First, exposure (charge storage) for acquiring a frame image of the Mth frame is started by applying a reset signal 150 to pixels of the first line. Subsequently, exposure of the pixels of each line is started by also applying the reset signal 150 in sequence to the pixels from the second line to the last line in a manner in which there is a delay of a predetermined time period in the application of the reset signal 150 to the respective lines.

When an exposure time that is determined in advance that is delayed by a predetermined time period in order from the first line to the last line, respectively, elapses, a read-out signal 152 that reads out a pixel signal from each pixel is applied in sequence to each line. As a result, accompanying the end of the exposure periods of the respective lines that end in sequence with a delay of a predetermined time therebetween, pixel signals of voltages corresponding to the charge amounts (exposure amounts) stored in the respective pixels are read out for each line.

Accordingly, the timings of exposure periods for acquiring a frame image of the Mth frame and the timings for reading out pixel signals are delayed by a predetermined time period for each line from the first line to the last line.

Similar driving is also performed when acquiring a frame image in the subsequent M+1th frame. According to the present embodiment, at a time of normal imaging (time of a normal imaging condition setting), if it is assumed that the number of frame images (frame rate) captured in one second by the image pickup element 58 is 60 fps (60 p), the start and end of exposure as well as reading out of pixel signals for each line is repeated every 1/60 sec.

In this connection, droplets scatter in the vicinity of the observation window 40 when spraying air or water from the air/water feeding nozzle 43, when sucking body fluids from the forceps outlet 20, and when spraying washing water or a liquid such as a dye at a site to be observed utilizing a predetermined channel (including a channel that is not shown in FIG. 2 and the like) such as the forceps channel.

If a scattered droplet traverses the range of field of view of the image pickup unit 54 at a high speed, the illuminating light is momentarily reflected by the droplet, and an image of the droplet (droplet image) is appears in the video (dynamic image).

Figure 5:
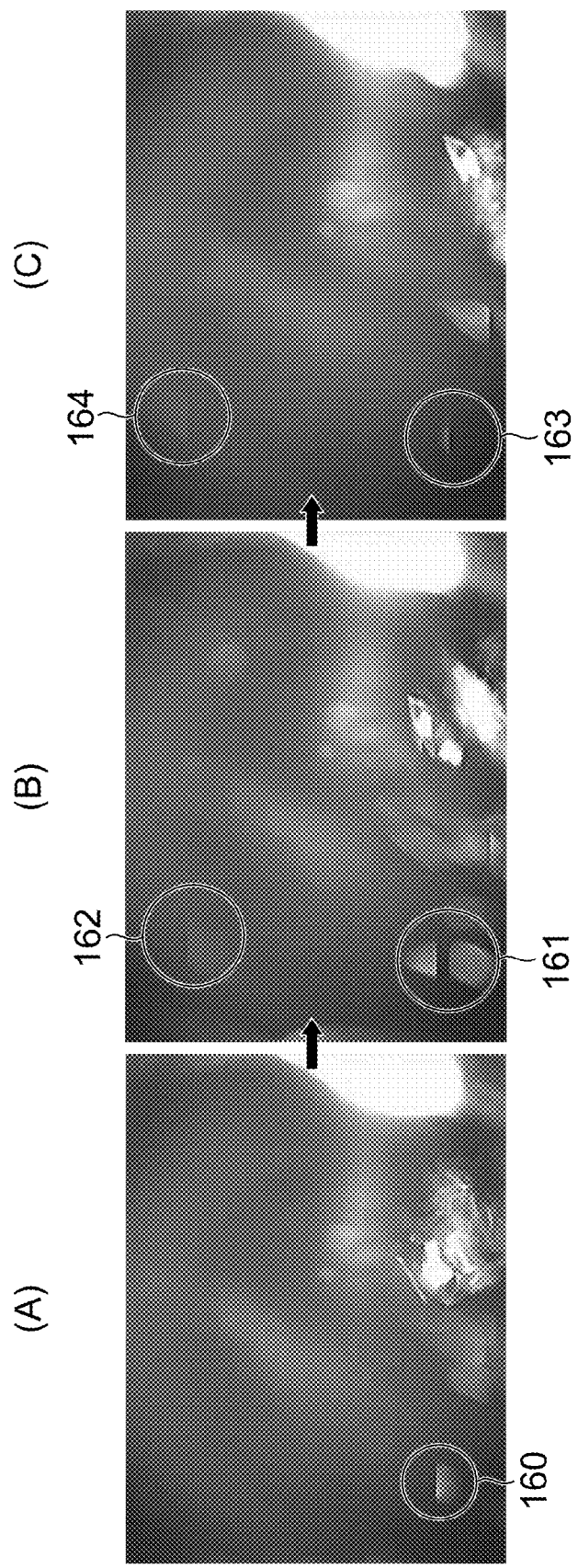
FIG. 5 is a view that illustrates frame images for three temporally adjacent frames that were actually imaged by an image pickup unit in a situation in which droplets were being scattered.
Figure 6:
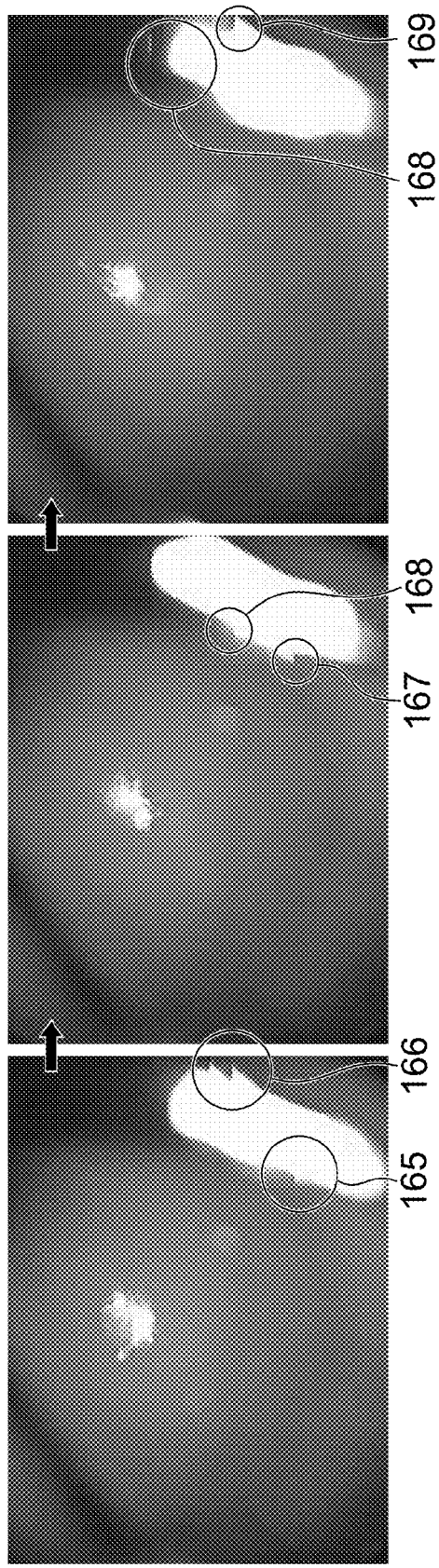
FIG. 6 is a view that illustrates frame images for three temporally adjacent frames that were actually imaged by an image pickup unit in a situation in which droplets were being scattered.

It has been confirmed that in such circumstances the following kind of unnatural video is observed. FIG. 5 and FIG. 6 are views that respectively illustrate, in sequential order, frame images for three temporally adjacent frames that were actually imaged by the image pickup unit 54 in a situation in which droplets were scattering.

As shown in FIG. 5 and FIG. 6, a linear unnatural edge arises along the horizontal direction in some droplet images that appear in each frame image. For example, droplet images that appear in regions designated by reference numerals 160 to 164 in the portions (A) to (C) of FIG. 5, and droplet images that appear in regions designated by reference numerals 165 to 169 in the portions (A) to (C) of FIG. 6 correspond to such a situation.

Figure 7:
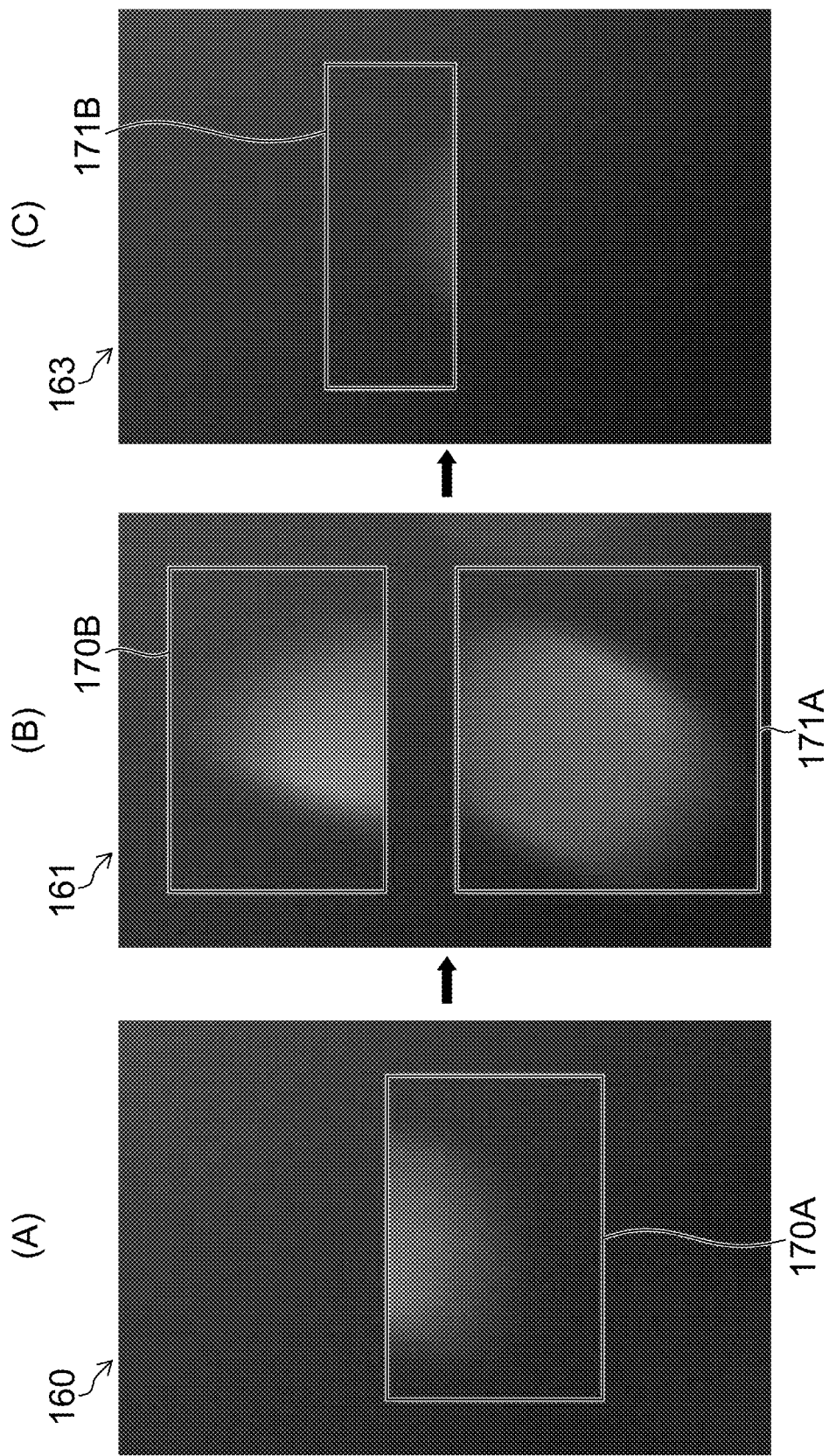
FIG. 7 is a view that illustrates, in an enlarged manner, the vicinity of the same position on a screen with respect to FIG. 5.

FIG. 7 is a view that, with respect to FIG. 5, illustrates, in an enlarged manner, the vicinity of regions 160, 161, and 163 that are at approximately the same position on the screen. As can be easily confirmed from FIG. 7, an unnatural edge in the horizontal direction arises on the upper side in a droplet image 170A in the portion (A) of FIG. 7 and a droplet image 171A in the portion (B) of FIG. 7, and an unnatural edge in the horizontal direction arises on the lower side in a droplet image 170B in the portion (B) of FIG. 7 and a droplet image 171B in the portion (C) of FIG. 7.

In the present specification, this phenomenon in which an unnatural edge is formed in a droplet image is referred to as an "edging phenomenon". This edging phenomenon has not been found in a case where the respective scan lines of an image pickup element are simultaneously exposed and frame images are acquired, for example, in a case where the global shutter method is adopted as a driving method of a CMOS type image pickup element or a case where a CCD image pickup element is used. Therefore, it is considered that the occurrence of the edging phenomenon is due to the fact that the driving method of the image pickup element 58 is the rolling shutter method.

In addition, because this phenomenon is found only in a situation in which droplets are being scattered, a characteristic of scattering droplets as an object is considered to be the cause of the phenomenon.

As the result of experiments and analysis that were performed in a manner that took the above described circumstances into consideration, the present inventors clarified that the mechanism described hereunder is the mechanism through which the edging phenomenon occurs.

Figure 8:
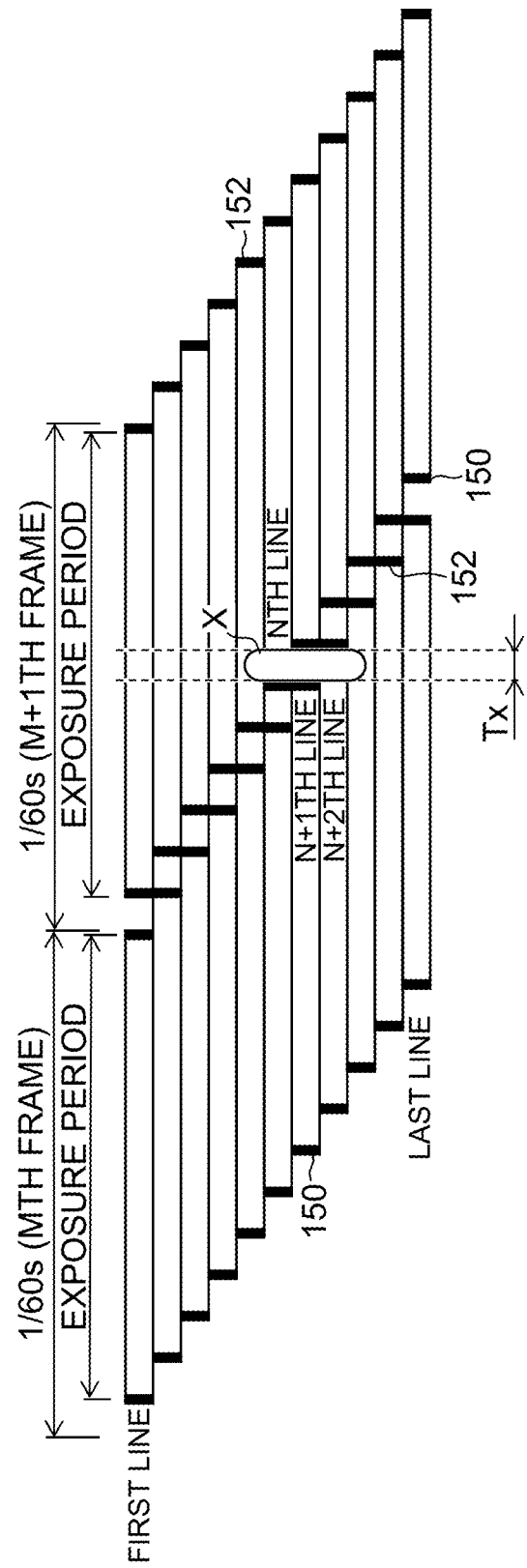
FIG. 8 is a similar view as FIG. 4, and is used to describe a mechanism by which an edging phenomenon occurs.

FIG. 8 is a view that, similarly to FIG. 4, shows the timing (exposure timing) of an exposure period for each line in a case of driving the image pickup element 58 by the rolling shutter method.

When driving the image pickup element 58 by the rolling shutter method and sequentially acquiring frame images, if a droplet that is being scattered passes through the range of field of view of the image pickup unit 54, the droplet traverses the range of field of view at a high speed and momentarily shines with a high luminance due to reflection of illuminating light. That is, the scattering droplet appears in the frame image as a high luminance droplet image for a short time only.

If it is assumed that a range in which the droplet appears within the frame image is, for example, a range including an area from an Nth line to an N+2th line as indicated by an area of droplet influence X in FIG. 8, a case can arise in which the droplet shines with a high luminance only during a non-exposure period of an N+1th line between two frames (the Mth frame and the M+1th frame) that are temporally adjacent. In FIG. 8, a period in which the droplet shines with a high luminance is represented as Tx, and it is assumed that the time period of the period Tx is shorter than that of the non-exposure period.

In a case where it is assumed the above situation arises, a high luminance droplet image will appear at a position of a line that is on the lower side relative to the N+1th line in the frame image of the Mth frame, and a high luminance droplet image will not appear at the position of the Nth line and lines on the upper side thereof. Further, it is surmised that a linear unnatural edge will arise along the horizontal direction on the upper side of the high luminance droplet image.

On the other hand, a high luminance droplet image will appear at a position of a line on the upper side relative to the N+1th line in the frame image of the M+1th frame that is the next frame after the Mth frame, and a high luminance droplet image will not appear at the position of the Nth line and lines on the lower side thereof. Further, it is surmised that a linear unnatural edge will arise along the horizontal direction on the lower side of the high luminance droplet image.

It is surmised that a droplet that exhibits high luminance only within the time of a non-exposure period of any line in this manner will be imaged as a droplet image that has been split between two frames, and this surmisation matches the appearance of droplet images that were actually observed.

Figure 9:
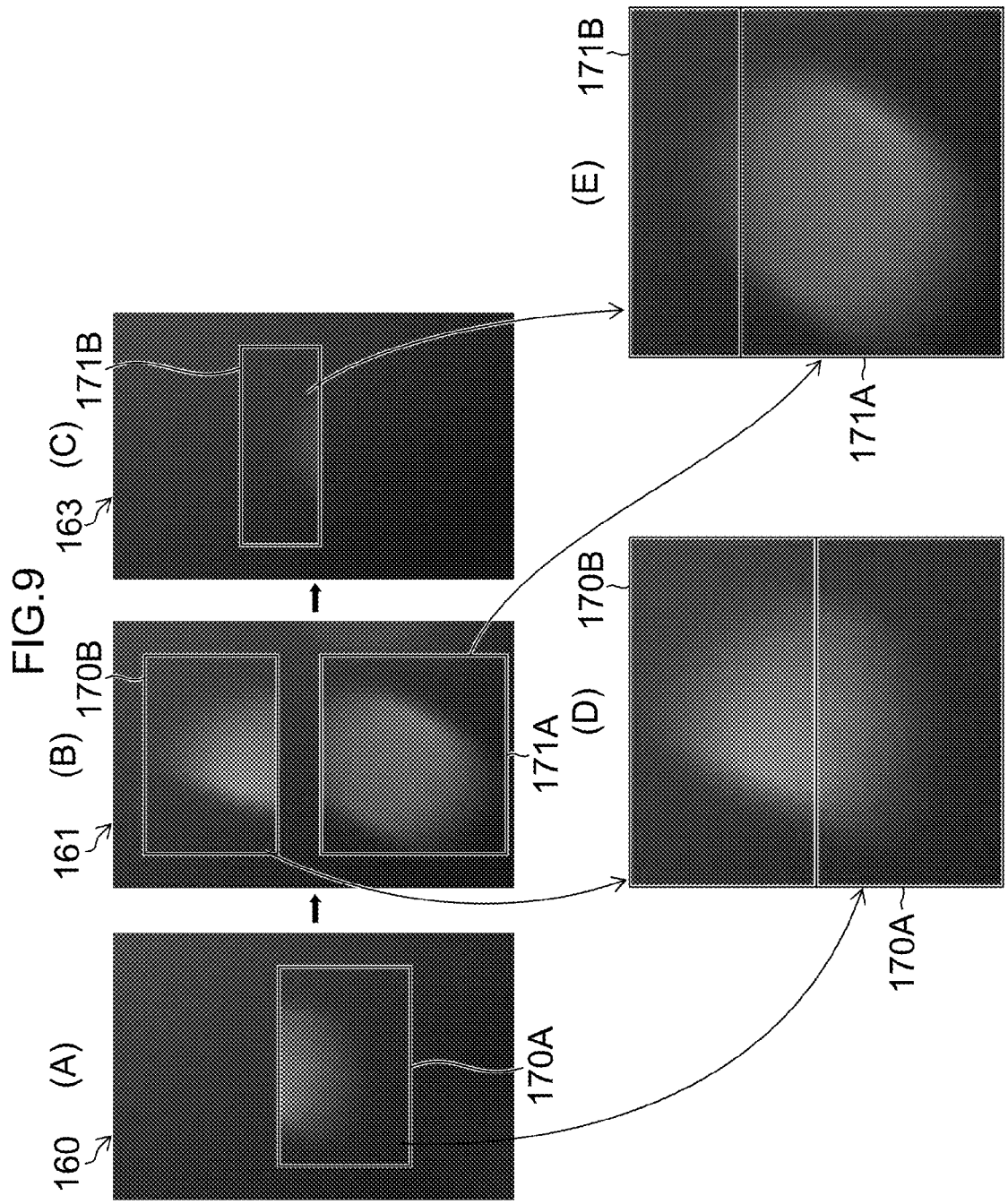
FIG. 9 is an explanatory drawing that is used in a description relating to the mechanism by which the edging phenomenon occurs.

For example, in FIG. 9 in which FIG. 7 that shows actually observed droplet images in an enlarged manner is represented as it is, the droplet image 170A that has an edge on an upper side in the portion (A) of FIG. 9 and the droplet image 170B that has an edge on a lower side in the portion (B) of FIG. 9 is consistent with the surmised appearance of droplet images described above. Further, the droplet image 171A that has an edge on an upper side in the portion (B) of FIG. 9 and the droplet image 171B that has an edge on a lower side in the portion (C) of FIG. 9 are also consistent with the surmised appearance of droplet images described above.

That is, if is assumed that a frame image when the image in the portion (A) of FIG. 9 was picked up is the frame image of the Mth frame in FIG. 8 and the frame image when the image in the portion (B) of FIG. 9 was picked up is the frame image of the M+1th frame in FIG. 8, the droplet image 170A in the portion (A) of FIG. 9 is consistent with the appearance of a droplet image that is surmised to arise in the frame image of the Mth frame in FIG. 8, and the droplet image 170B in the portion (B) of FIG. 9 is consistent with the appearance of a droplet image that is surmised to arise in the frame image of the M+1th frame in FIG. 8.

In addition, when the droplet image 170A in the portion (A) of FIG. 9 and the droplet image 170B in the portion (B) of FIG. 9 are synthesized without altering the respective positions of the droplet images on the screen, a droplet image that can be regarded as a single image is formed as shown in the portion (D) of FIG. 9, and it is thus found that the droplet images 170A and 170B are images obtained as the result of an image of a droplet that was originally a single mass being split into upper and lower parts across two frames.

Similarly, if it is assumed that a frame image when the image in the portion (B) of FIG. 9 was picked up is the frame image of the Mth frame in FIG. 8 and the frame image when the image in the portion (C) of FIG. 9 was picked up is the frame image of the M+1th frame in FIG. 8, the droplet image 171A in the portion (B) of FIG. 9 is consistent with the appearance of a droplet image that is surmised to arise in the frame image of the Mth frame in FIG. 8, and the droplet image 171B in the portion (C) of FIG. 9 is consistent with the appearance of a droplet image that is surmised to arise in the frame image of the M+1th frame in FIG. 8.

Further, when the droplet image 171A in the portion (B) of FIG. 9 and the droplet image 171B in the portion (C) of FIG. 9 are synthesized without altering the respective positions of the droplet images on the screen, a droplet image that can be regarded as a single image is formed as shown in the portion (E) of FIG. 9, and it is thus found that the droplet images 171A and 171B are images obtained as the result of an image of a droplet that was originally a single mass being split into upper and lower parts across two frames.

Based on the foregoing, it is considered that the edging phenomenon as illustrated in FIG. 9 is a phenomenon that arises due to a droplet exhibiting a high luminance only during the time of a non-exposure period of any line as shown in FIG. 8.

That is, it is considered that since reflected light from an object that is moving at a high speed arises only in an extremely short time period, a scan line group in which the object that is moving at a high speed appears and a scan line group in which the object that is moving at a high speed does not appear arise, and the cause of the occurrence of the edging phenomenon is that a boundary portion between the aforementioned scan line groups is recognized as an edge along a direction parallel to the scan lines.

Further, in FIG. 5 and FIG. 6, among the droplet images having an edge in the horizontal direction, there are also some droplet images whose form does not necessarily match the droplet images in FIG. 9. Although the reasons that can be considered for these differences in form include that a plurality of droplet images overlapped with each other, that one droplet only partially entered the state described using FIG. 8, or that a high luminance droplet arose that spanned the exposure period of both or one of the Mth frame and the M+1th frame, fundamentally it is considered that a droplet image having an unnatural edge in a horizontal direction occurs due to the reason that was described in the foregoing.

Next, processing that is executed to mitigate the effect of above described edging phenomenon in the endoscope system 10 of the present embodiment is described.

Figure 10:
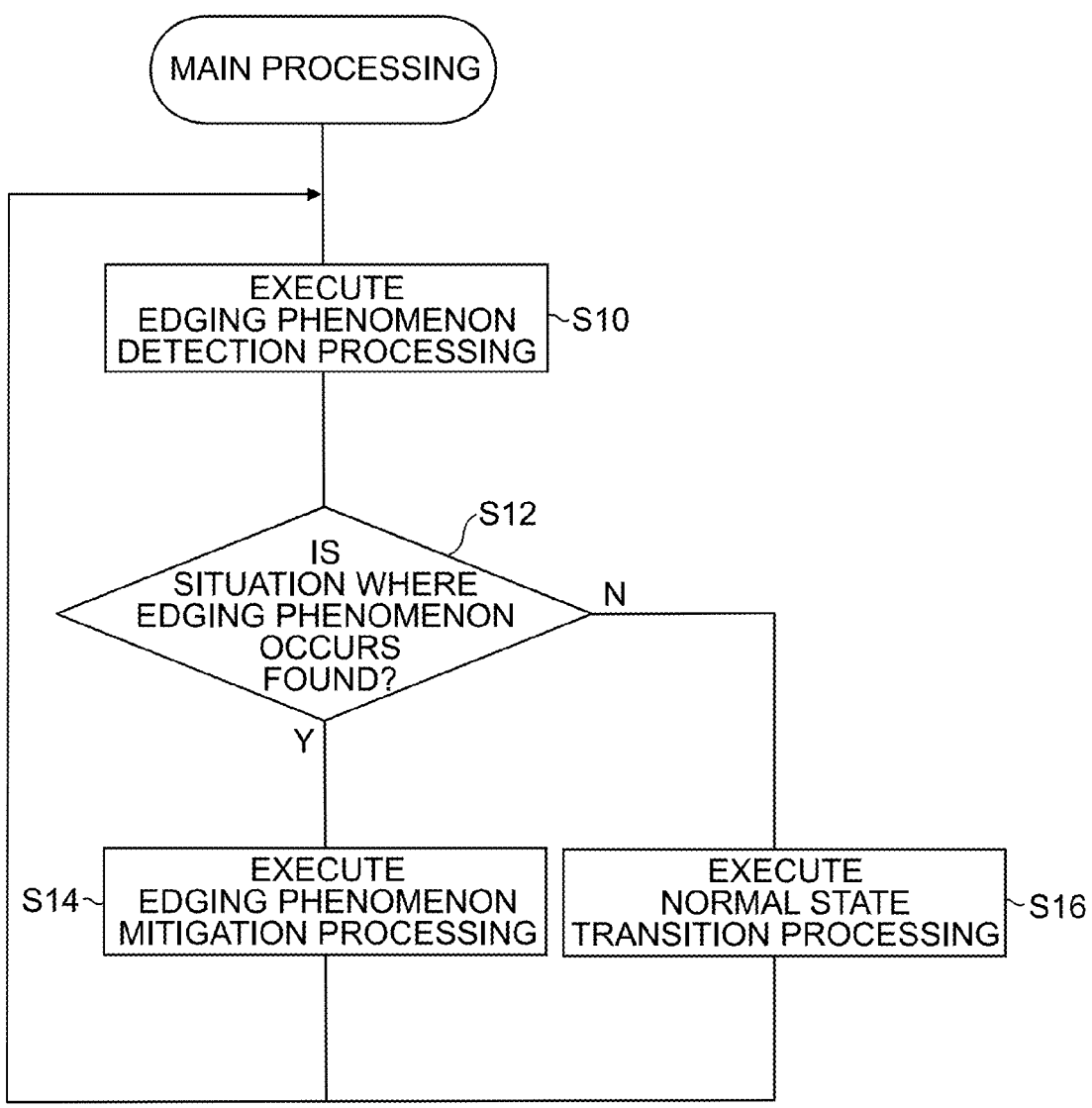
FIG. 10 is a flowchart that illustrates an outline of overall processing for edging phenomenon mitigation.

FIG. 10 is a flowchart that illustrates an outline of the overall processing for edging phenomenon mitigation.

A CPU 82 (see FIG. 3) of the processor apparatus 12 first executes edging phenomenon detection processing for detecting a situation in which the edging phenomenon occurs, as processing in step S10.

Here, the term "detecting a situation in which the edging phenomenon occurs" refers to detecting a situation in which the edging phenomenon is actually occurring, or to detecting a situation in which it is possible for the edging phenomenon to occur.

For example, a case where an edge in the horizontal direction of a droplet image was detected is a situation in which the edging phenomenon is occurring, and detection of an edge in the horizontal direction of a droplet image can be taken as one form (form (1) that is described later) of the edging phenomenon detection processing.

Further, a case where a situation is detected in which droplets are scattering within the range of the field of view is a situation in which the edging phenomenon is almost occurring at a time of normal imaging (time of a normal imaging condition setting), and detection of a situation in which droplets are scattering within the range of the field of view can also be taken as one form (form (2) that is described later) of the edging phenomenon detection processing.

Further, in a case where a specific operation in which it is possible for droplets to be scattered within the range of the field of view is being performed by a surgeon or the like, such as when feeding of water or the like from the air/water feeding nozzle 43 is performed, because such a situation can be considered to be one in which the possibility of the edging phenomenon occurring is extremely high, detection of the performance of such an operation can also be taken as one form (form (3) that is described later) of the edging phenomenon detection processing.

Next, as the processing in step S12, based on the result of the edging phenomenon detection processing in step S10, the CPU 82 determines whether or not the situation where the edging phenomenon occurs is found. If the CPU 82 determined that the situation where the edging phenomenon occurs is found (result is "yes"), the process transitions to step S14, while if the CPU 82 determined that the situation where the edging phenomenon occurs is not found (result is "no"), the process transitions to step S16.

Note that the processing performed by the CPU 82 in steps S10 and S12 corresponds to processing of a detection device that detects whether or not an image region that is edged along a direction parallel to a scan line exists in a frame image that is obtained by the image pickup element 58.

In the processing in step S14, edging phenomenon mitigation processing is executed to mitigate the effect of the edging phenomenon.

As described in detail later, a form that executes predetermined processing on frame images that were sequentially imaged by the image pickup unit 54, or a form that changes an operation (an exposure time or driving method) of the image pickup element 58 or the like can be adopted as the edging phenomenon mitigation processing.

In the processing in step S16, normal state transition processing is executed for transitioning to a state at a time of normal imaging in which the edging phenomenon mitigation processing is not executed.

In this case, the normal state transition processing also includes simply not executing the edging phenomenon mitigation processing (entering the state at the time of normal imaging).

When the above described processing in step S14 or step S16 ends, the CPU 82 returns to the processing in step S10. The CPU 82 then repeats the processing from step S10.

Next, a specific form of the edging phenomenon mitigation processing in step S14 of FIG. 10 will be described.

Any of the following form (a), form (b), and form (c) can be adopted as the form of edging phenomenon mitigation processing. Specific processing contents of these three forms are described in order hereunder.

The edging phenomenon mitigation processing of form (a) blurs edges in a horizontal direction of a droplet image that arose as shown in the portion (A) of FIG. 11 as the edging phenomenon in frame images that are imaged in sequence by the image pickup unit 54, by filter processing (blurring processing) as shown in the portion (B) of FIG. 11. It is thereby possible to decrease abrupt changes in pixel values in the vertical direction at edges in the horizontal direction of the droplet images, and thus mitigate the effects of the edging phenomenon.

Figure 12:
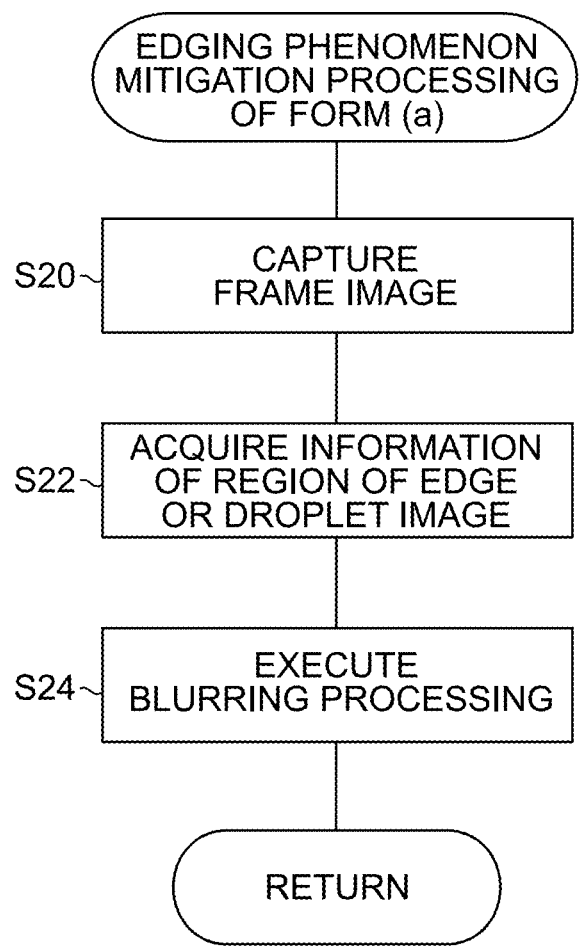
FIG. 12 is a flowchart that illustrates procedures of the edging phenomenon mitigation processing of form (a)

The edging phenomenon mitigation processing according to form (a) can be performed, for example, by the CPU 82 of the processor apparatus 12 shown in FIG. 3 acquiring image data of frame images imaged by the image pickup unit 54 from the DSP 86. More specifically, the processing is executed in the following manner in accordance with the procedures of the flowchart shown in FIG. 12.

The present edging phenomenon mitigation processing according to form (a) is executed in step S14 in a case where a situation in which the edging phenomenon occurs was detected by the edging phenomenon detection processing in step S10 and the determination processing in step S12 of FIG. 10. First, as the processing in step S20, the CPU 82 captures image data of frame images imaged by the image pickup unit 54 that was generated by the DSP 86 of the processor apparatus 12.

However, in a case where the CPU 82 captures image data of frame images in the same manner as this in the edging phenomenon detection processing in step S10, the image data captured at that time can be used in the present edging phenomenon mitigation processing in step S14 and it is not necessary to capture the image data once again.

Next, as the processing in step S22, the CPU 82 acquires information regarding an edge in a horizontal direction of a droplet image or an image region of a droplet image in a frame image. This information may be obtained by referring to information detected when performing the edging phenomenon detection processing in step S10. In a case where such information is not obtained in the edging phenomenon detection processing, as the processing in the present step S22, the CPU 82 may detect the information by performing image processing with respect to the present frame image. Such image processing is described later along with a description of a specific form of the edging phenomenon detection processing.

Subsequently, as the processing in step S24, the CPU 82 (an image blurring device included in the CPU 82) executes blurring processing with respect to the edge in the horizontal direction of the droplet image or the image region of the droplet image in the frame image.

This blurring processing may be blurring in only the vertical direction, or may be blurring in both the vertical and horizontal directions.

Further, an image region on which the blurring processing is executed can be an image region of an edge periphery along an edge that includes the position of the edge in the horizontal direction of the droplet image, or can be an image region around a droplet image that includes the entire droplet image, and it is sufficient if the image region is of a range such that at least the edge in the horizontal direction can be blurred.

When blurring processing is executed with respect to the frame image as described above and the edging phenomenon mitigation processing ends, the CPU 82 outputs the image data of the frame image on which the blurring processing was performed to the display control circuit 88 to cause the frame image to be displayed on the monitor 27.

On the other hand, according to the normal state transition processing in step S16 in a case where it was detected that the situation where the edging phenomenon occurs is not found by means of the edging phenomenon detection processing in step S10 and the determination processing in step S12 of FIG. 10, the above described edging phenomenon mitigation processing is not executed, and the CPU 82 outputs the image data of the frame image on which blurring processing was not performed to the display control circuit 88 to cause the frame image to be displayed on the monitor 27.

Note that it is also possible to perform the above described edging phenomenon mitigation processing of form (a) at the DSP 86 or at another image processing unit based on an instruction from the CPU 82.

The edging phenomenon mitigation processing of form (b) mitigates the effects of the edging phenomenon by lengthening the exposure time at the image pickup element 58 (delaying the shutter speed).

The reason that the effect of the edging phenomenon can be mitigated by lengthening the exposure time will now be described.

Figures 13A, 13B:
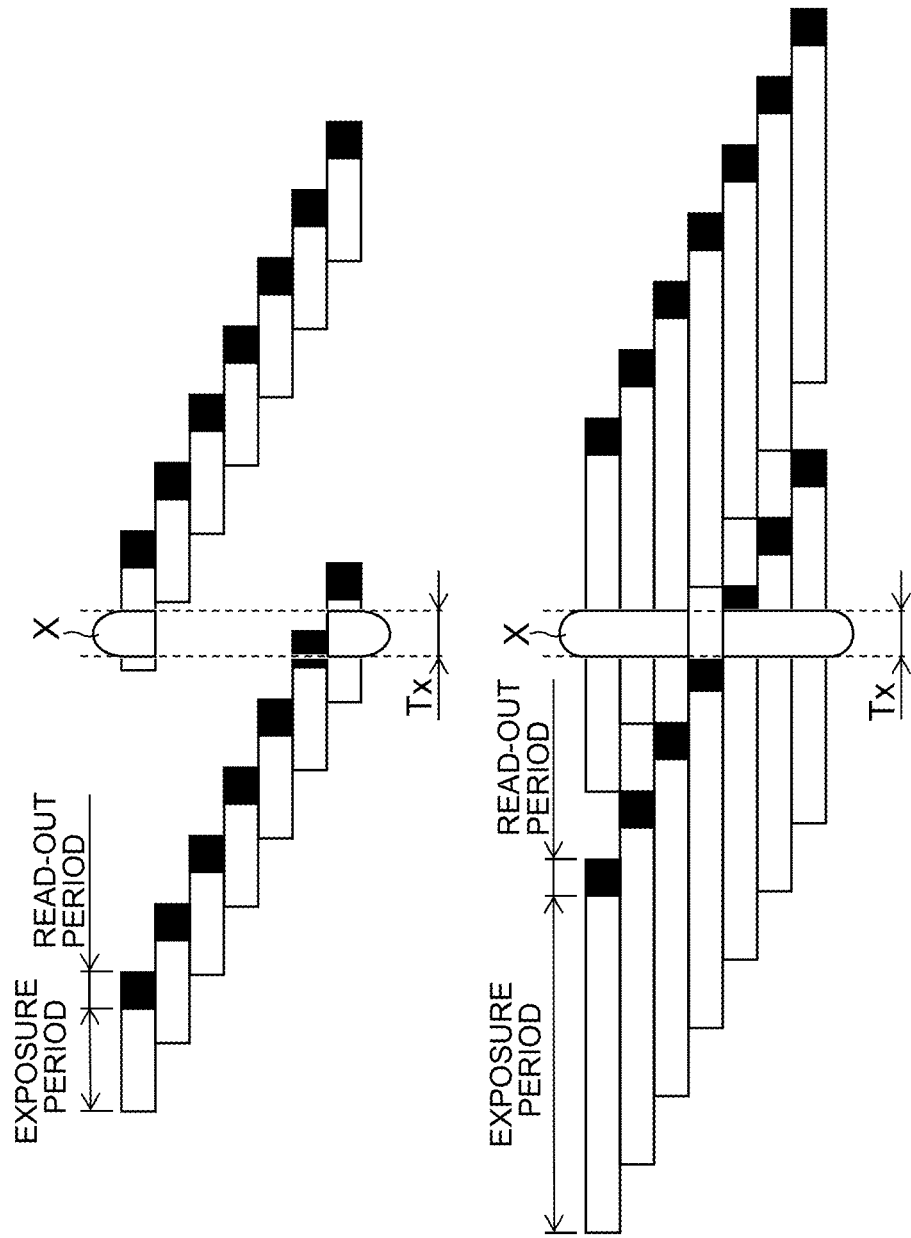

FIGS. 13A and 13B are views that focus on and illustrate the timing of an exposure period (charge storage period) of each line of the image pickup element 58 and a pixel signal read-out period with respect to only two frames that are temporally adjacent, and show that a high luminance droplet with an area of droplet influence X arises in a time period Tx that is shorter than a non-exposure period. FIG. 13A illustrates a case where the exposure time is $\frac{1}{200}$ sec, and FIG. 13B illustrates a case where the exposure time is $\frac{1}{60}$ sec which is a longer exposure time than in FIG. 13A.

As shown in FIGS. 13A and 13B, between two temporally adjacent frames, the number of lines that enter a non-exposure period at the same time increases as the exposure time is shortened.

In contrast, at a time of normal imaging when edging phenomenon mitigation processing is not executed (time of a normal imaging condition setting), in order to obtain a dynamic image of high image quality, the exposure time is set to a comparatively short time period, for example, a period of $\frac{1}{200}$ sec as in FIG. 13A.

In a case where the edging phenomenon occurs at a time of normal imaging, that is, a case where only a lower-side portion of a high luminance droplet appears in the frame image of the former frame among two temporally adjacent frames and only an upper-side portion of the high luminance droplet is appears in the frame image of the latter frame among the two temporally adjacent frames, the larger that the number of lines which enter a non-exposure period at the same time is, the greater the distance in the vertical direction is that separates the positions of droplet images corresponding to a single droplet that was split into two images.

If such frame images are displayed in order as a dynamic image on the screen of the monitor 27, the observer will visually recognize the droplet image on the lower side in the frame image of the former frame and the droplet image on the upper side in the frame image of the latter frame at approximately the same time.

At such time, the shorter that the exposure time is, the greater the degree to which the observer will visually recognize the two droplet images obtained as the result of the single droplet being split vertically with a large distance between the resulting two droplet images, and furthermore, the greater the degree to which a gap image with low luminance that arises in a linear shape in the horizontal direction between the separated droplet images will be visually recognized clearly. Accordingly, the images are easily perceived as the edging phenomenon.

In contrast, if the exposure time is made longer than at a time of normal imaging, for example, if it is assumed that the exposure time is changed to $\frac{1}{60}$ sec as shown in FIG. 13B, even in a case where the edging phenomenon occurred, the droplet images with respect to a single droplet appear in frame images of two frames that are temporally adjacent in a manner in which the droplet images are split at positions that are almost not separated from each other in the vertical direction that are in accordance with an amount that corresponds to a decrease in the number of lines that enter a non-exposure period at the same time.

In a case where such frame images are displayed in order as a dynamic image on the screen of the monitor 27 and an observer visually recognizes the droplet image on the lower side in the frame image of the former frame and the droplet image on the upper side in the frame image of the latter frame at approximately the same time, almost none of the continuity of the droplet images that have been split into upper and lower images with respect to the single droplet will be lost and the observer will visually recognize the droplet images as a single droplet image.

Accordingly, by lengthening the exposure time it is possible to obtain images in which it is difficult to perceive the edging phenomenon, and consequently the effect of the edging phenomenon can be mitigated.

In addition, another reason that the effect of the edging phenomenon can be mitigated by lengthening the exposure time is that when pixels of each line in the same frame receive light from a plurality of droplets that randomly arise during the exposure period of each line, a difference between the received light amounts of the respective lines decreases as the exposure time increases.

Figure 14:
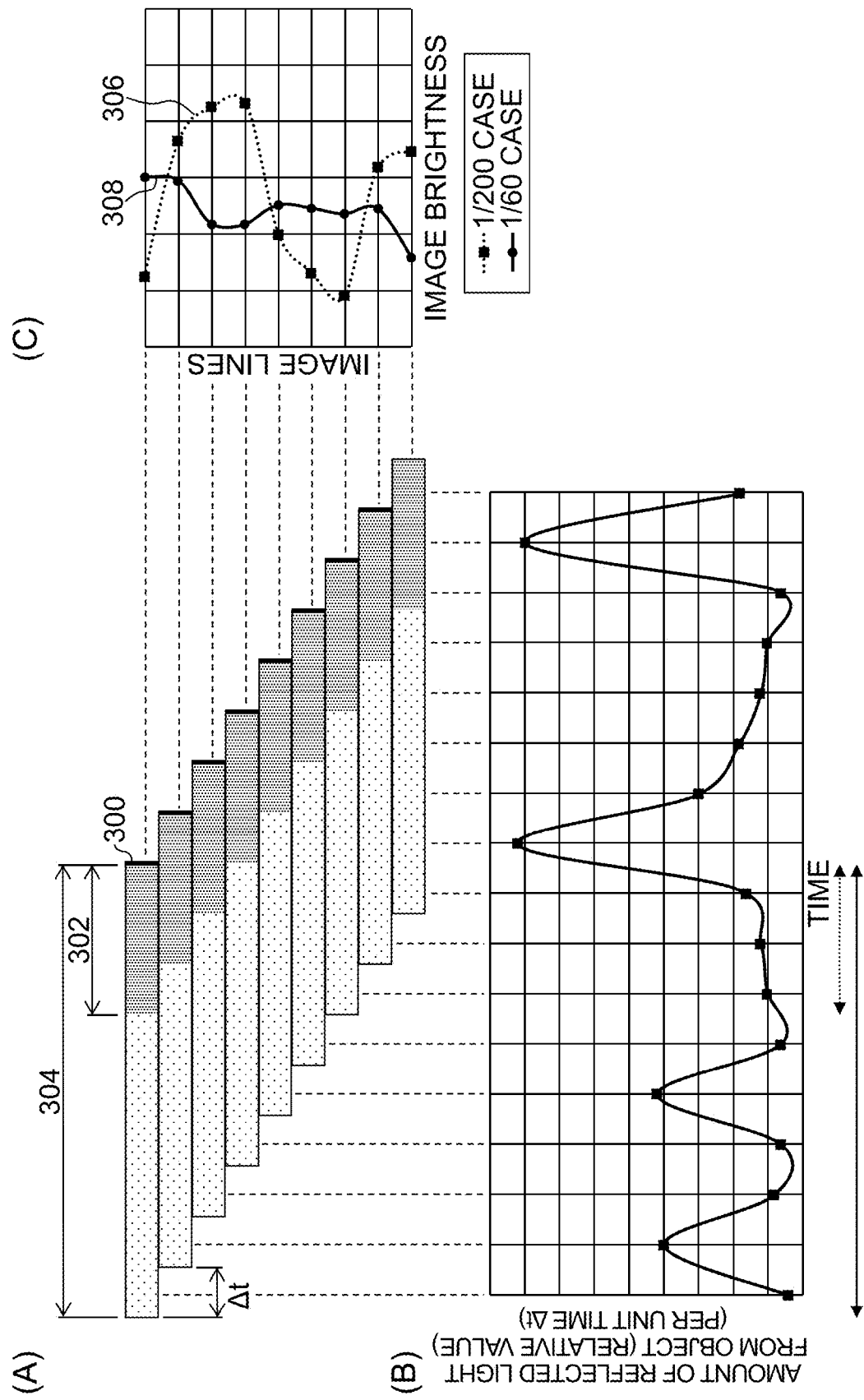
FIG. 14 is a view that illustrates the brightness of images of respective lines in a case where light of the same amount that fluctuates with time is made incident on the pixels of each line and illustrates a comparison between a case where, as the timing of the exposure period, an exposure time is 1/200 sec and a case where the exposure time is 1/60 sec.

FIG. 14 is a view that illustrates the brightness of images of respective lines in a case where light of the same amount that fluctuates with time is made incident on the pixels of each line and illustrates a comparison between a case where, as the timing of the exposure period, an exposure time is $\frac{1}{200}$ sec and a case where the exposure time is $\frac{1}{60}$ sec;

The timing of exposure periods for each line for one frame is shown in the portion (A) of FIG. 14 on the upper left in the drawing, and a case is illustrated in which the timing of an exposure period 302 of each line when the exposure time is $\frac{1}{200}$ sec and the timing of an exposure period 304 of each line when the exposure time is $\frac{1}{60}$ sec are matched with a timing 300 for reading out pixel signals.

On the other hand, a reflected light amount from an object per unit time Δt that is incident on the pixels of each line is shown in the portion (B) of FIG. 14 on the lower left in the drawing. The unit time Δt shows the amount of deviation between the times of starting exposure (resetting) of adjacent lines.

In a case where, within the time periods of the respective exposure periods shown in the portion (A) of FIG. 14, the pixels of each line receive light of a reflected light amount that changes as shown in the portion (B) of FIG. 14 at the respective times, and images are generated in accordance with the received light amounts (total amounts) that were received in the exposure periods, the brightness of the images of the respective lines is as shown in a graph in the portion (C) of FIG. 14 on the upper right in the drawing. In the portion (C) of FIG. 14, the case where the exposure time is $1/200$ sec is represented by a curve 306, and the case where the exposure time is $1/60$ sec is represented by a curve 308.

It is thus is found that in comparison to a case where the exposure time is a short time period of $1/200$ sec, when the exposure time is a long time period of $1/60$ sec there is less difference between the brightness of the images for each line. Accordingly, when the exposure time is lengthened, the individual droplet images become blurred, and instead of the image quality decreasing, the effect of the edging phenomenon can be mitigated.

Figure 15:
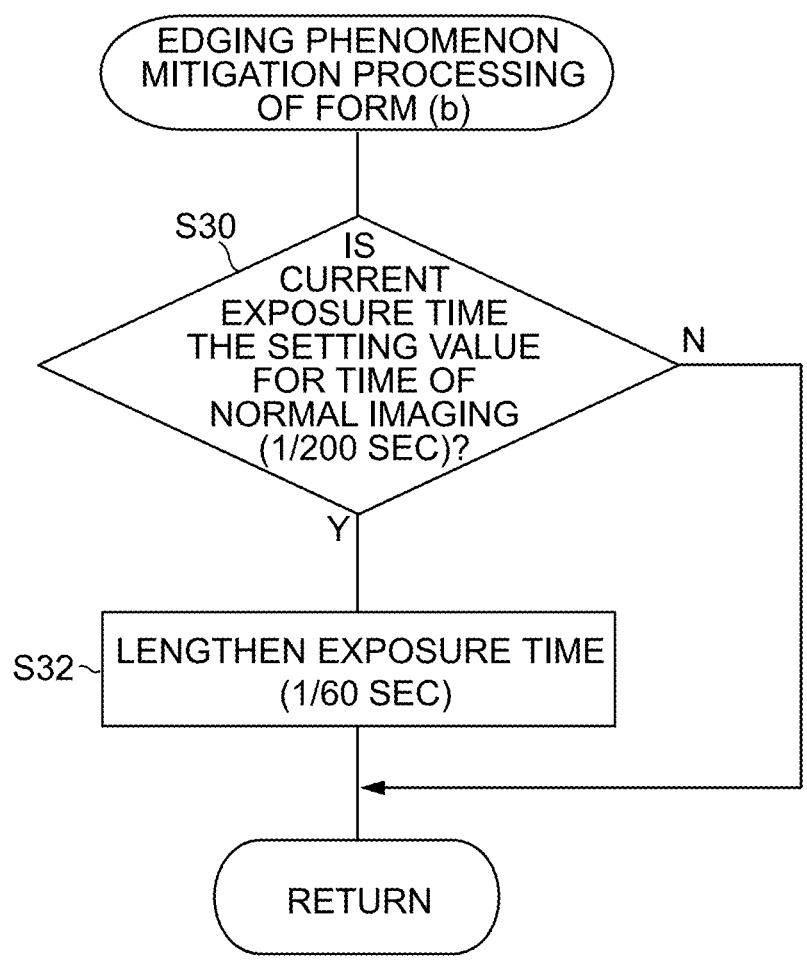
FIG. 15 is a flowchart that illustrates procedures of edging phenomenon mitigation processing of form (b)

For example, the CPU 82 of the processor apparatus 12 shown in FIG. 3 can perform the above described edging phenomenon mitigation processing of form (b), as an exposure control device, by instructing the image pickup unit 54 to change the exposure time (shutter speed) of the image pickup element 58 through the CPU 80 of the endoscope 11. More specifically, the edging phenomenon mitigation processing of form (b) is executed in the following manner in accordance with the procedures in the flowchart of FIG. 15.

The present edging phenomenon mitigation processing of form (b) is executed in step S14 of FIG. 10 when it is detected that the situation where the edging phenomenon occurs is found by means of the edging phenomenon detection processing in step S10 and the determination processing in step S12 of FIG. 10. First, as the processing in step S30, the CPU 82 determines whether or not the current exposure time is set to $1/200$ sec as the exposure time at a time of normal imaging.

If the result determined in step S30 is "yes", as the processing in step S32, the CPU 82 instructs the image pickup unit 54 to change the exposure time to, for example, $1/60$ sec, and drives the image pickup element 58 using the exposure time that is longer than at a time of normal imaging.

In contrast, if the result determined in step S30 is "no", since the exposure time is already set to $1/60$ sec, the CPU 82 does not issue an instruction to change the exposure time.

Thus, the edging phenomenon mitigation processing ends.

Figure 16:
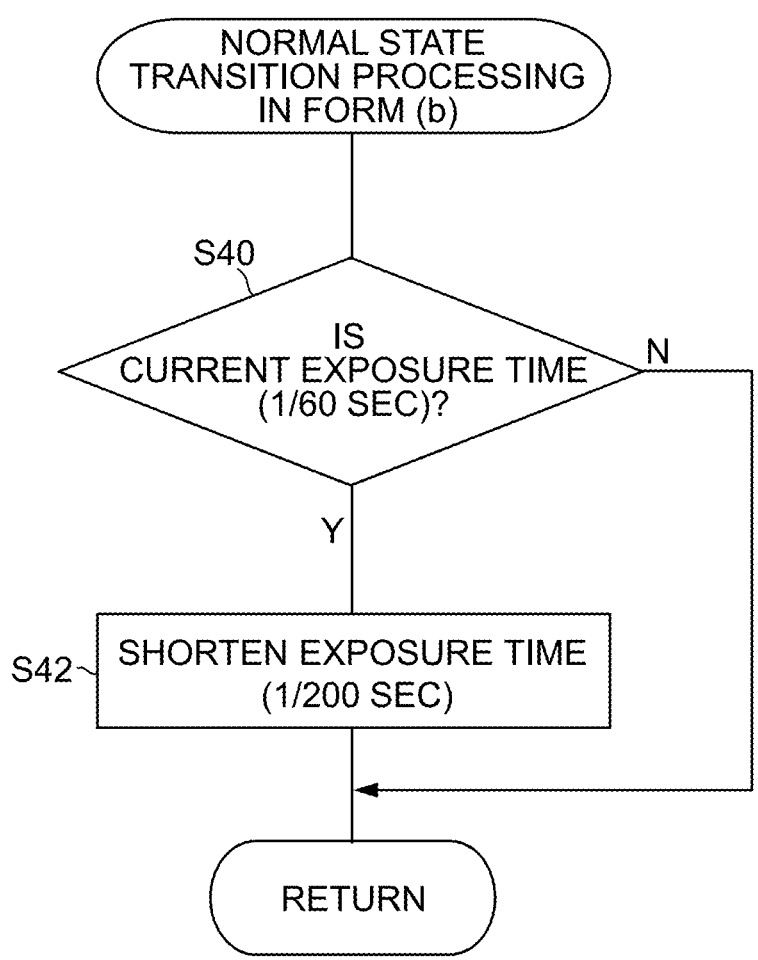
FIG. 16 is a flowchart that illustrates procedures of normal state transition processing in a case where the edging phenomenon mitigation processing of form (b) is adopted.

Next, the normal state transition processing in step S16 in FIG. 10 in a case where the edging phenomenon mitigation processing of form (b) is adopted will be described using the flowchart in FIG. 16.

The normal state transition processing in step S16 of FIG. 10 is executed when it is detected that the situation where the edging phenomenon occurs is not found by means of the edging phenomenon detection processing in step S10 and the determination processing in step S12 of FIG. 10. First, as the processing in step S40, the CPU 82 determines whether or not the current exposure time is set to $1/60$ sec that is the exposure time changed to in the above described step S32.

If the result determined in step S40 is "yes", as the processing in step S42, the CPU 82 instructs the image pickup unit 54 to change the exposure time to $1/200$ sec as the exposure time for a time of normal imaging, and drives the image pickup element 58 using the exposure time for a time of normal imaging. Consequently, the imaging operation returns to imaging with high image quality for a time of normal imaging.

In contrast, if the result determined in step S40 is "no", since the exposure time is already set to $1/200$ sec, the CPU 82 does not issue an instruction to change the exposure time.

By performing the above described edging phenomenon mitigation processing and normal state transition processing, when it is detected that the situation where the edging phenomenon occurs is found, the exposure time can be lengthened relative to a time of normal imaging to thereby mitigate the effect of the edging phenomenon, while when it is detected that the situation is not one is which the edging phenomenon occurs, the exposure time can be restored to the exposure time at the time of normal imaging to thereby return to imaging with high image quality.

Note that, when lengthening the exposure time, the exposure time can also be made another value that is longer than the exposure time at the time of normal imaging, and not the value of $1/60$ sec. The exposure time at the time of normal imaging is also not limited to $1/200$ sec as described above.

Figure 17:
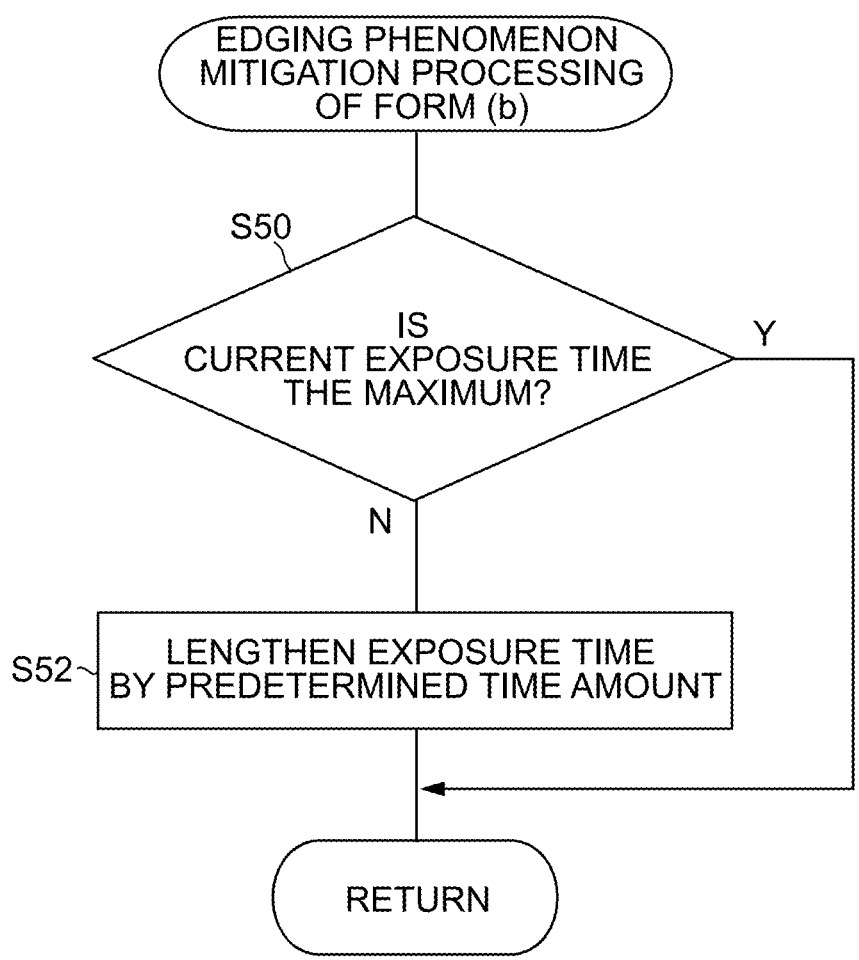
FIG. 17 is a flowchart that illustrates other procedures of the edging phenomenon mitigation processing of form (b)

Further, a configuration may also be adopted so that, each time it is detected that the situation where the edging phenomenon occurs is found by means of the edging phenomenon detection processing in step S10 and the determination processing in step S12, in the edging phenomenon mitigation processing in step S14, the exposure time is gradually (in incremental steps) lengthened in a range from the exposure time at the time of normal imaging to the maximum (upper limit of the changeable range) exposure time. FIG. 17 is a flowchart illustrating procedures in this case.

When the edging phenomenon mitigation processing of form (b) in step S14 of FIG. 10 starts, as the processing in step S50, the CPU 82 determines whether or not the current exposure time is set to the maximum exposure time.

If the result determined in step S50 is "no", as the processing in step S52, the CPU 82 instructs the image pickup unit 54 to change the exposure time to an exposure time that is longer by the amount of a predetermined time period relative to the current exposure time.

If the result determined in step S50 is "yes", the CPU 82 does not issue an instruction to the image pickup unit 54 to change the exposure time.

Thus, the exposure time can be gradually increased each time it is detected that the situation where the edging phenomenon occurs is found.

Figure 18:
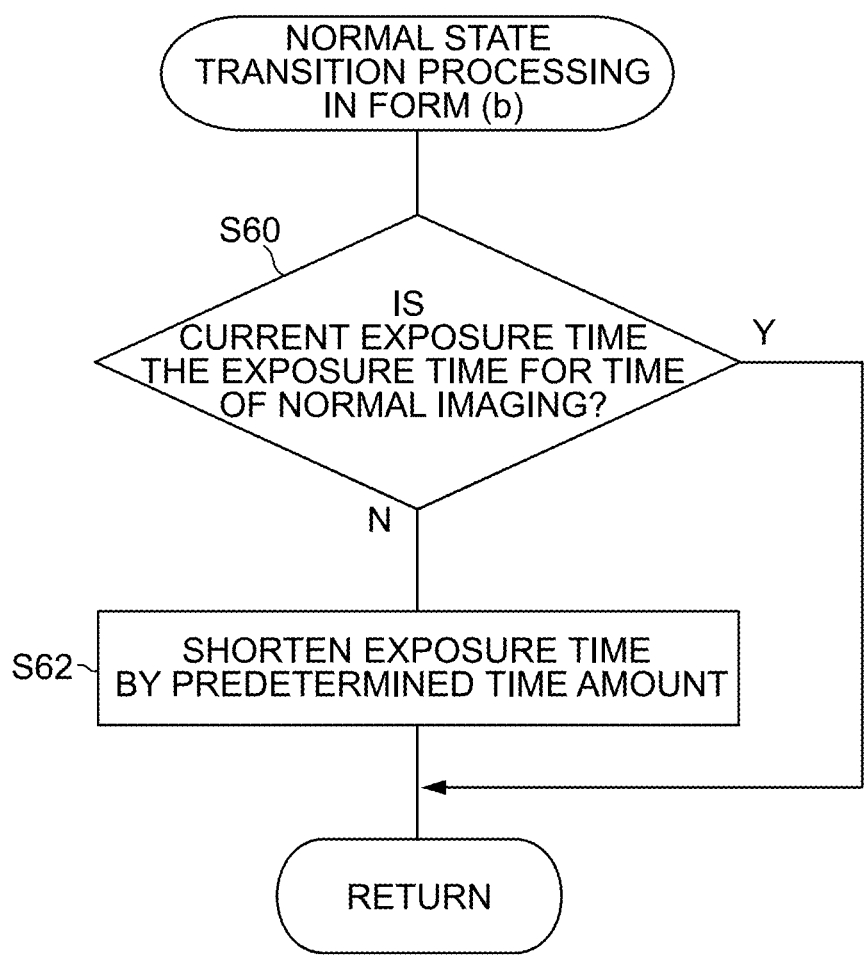
FIG. 18 is a flowchart that illustrates procedures of normal state transition processing in a case where the edging phenomenon mitigation processing of form (b) is adopted.

Similarly, a configuration may also be adopted so that, each time it is detected that the situation where the edging phenomenon occurs is not found by means of the edging phenomenon detection processing in step S10 and the determination processing in step S12 of FIG. 10, in the normal state transition processing in step S16, the exposure time is gradually shortened as far as the exposure time at the time of normal imaging. FIG. 18 is a flowchart illustrating procedures in this case.

When the normal state transition processing in step S16 of FIG. 10 starts, as the processing in step S60, the CPU 82 determines whether or not the current exposure time is set to the exposure time for a time of normal imaging.

If the result determined in step S60 is "no", as the processing in step S62, the CPU 82 instructs the image pickup unit 54 to change the exposure time to an exposure time that is shorter by the amount of a predetermined time period relative to the current exposure time.

If the result determined in step S60 is "yes", the CPU 82 does not issue an instruction to the image pickup unit 54 to change the exposure time.

Thus, the exposure time can be gradually shortened each time it is detected that the situation where the edging phenomenon occurs is not found.

Instead of giving rise to a decrease in image quality, the edging phenomenon mitigation processing of form (c) completely suppresses the edging phenomenon by switching to driving by a pseudo-global shutter method in contrast to driving the image pickup element 58 by the rolling shutter method as shown in FIG. 4 at a time of normal imaging. Note that it was confirmed that the edging phenomenon arises only when the image pickup element 58 is driven by the rolling shutter method as described above, and does not arise when the image pickup element 58 is driven by the global shutter method.

In this case, in the rolling shutter method at the time of normal imaging illustrated in FIG. 4, the frame rate in the progressive format (scanning format) is 60 fps (60 p). Note that, as described above, the exposure time is set to, for example, a comparatively short time of 1/200 sec, and does not necessarily match the aforementioned drawing.

Figure 19:
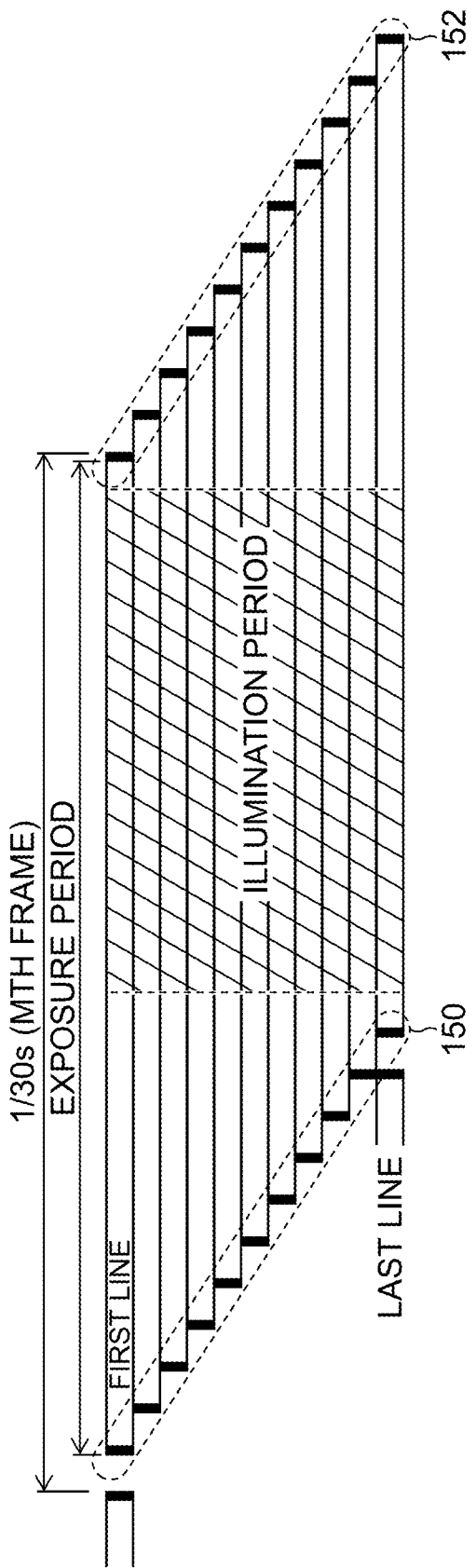
FIG. 19 is a view that is used to describe edging phenomenon mitigation processing of form (c), which illustrates a case where the image pickup element is switched to driving (30 p) using a pseudo-global shutter method.

In contrast, according to the pseudo-global shutter method, as shown in FIG. 19, the shutter method is switched to a rolling shutter method in which the frame rate in the progressive format is 30 fps (30 p). Further, the exposure time is set to, for example, a maximum exposure time of 1/30 sec.

As a result, in the same frame, a long time period in which all lines from the first line to the last line enter an exposure state is secured. Note that the exposure time need not necessarily be set to the maximum exposure time, and it is sufficient for the exposure time to be a value such that a predetermined time period or more is secured with respect to a period in which all lines simultaneously enter an exposure state.

Further, illuminating light that is supplied to the endoscope 11 from the light source apparatus 13 is switched from continuous illumination for a time of normal imaging to intermittent illumination (intermittent light emission), and as shown as an illumination period in FIG. 19, illuminating light is irradiated at a site to be observed only in a time period in which all lines are in an exposure state.

As a result, although the driving of the image pickup element 58 is performed according to the rolling shutter method, since charge storage is not performed other than in an illumination period, imaging can be performed that is equivalent to a case where the image pickup element 58 is driven by the global shutter method when the frame rate in the progressive format is 30 fps, and instead of leading to a decline in the image quality in comparison to a time of normal imaging, the edging phenomenon can be completely suppressed.

Figure 20:
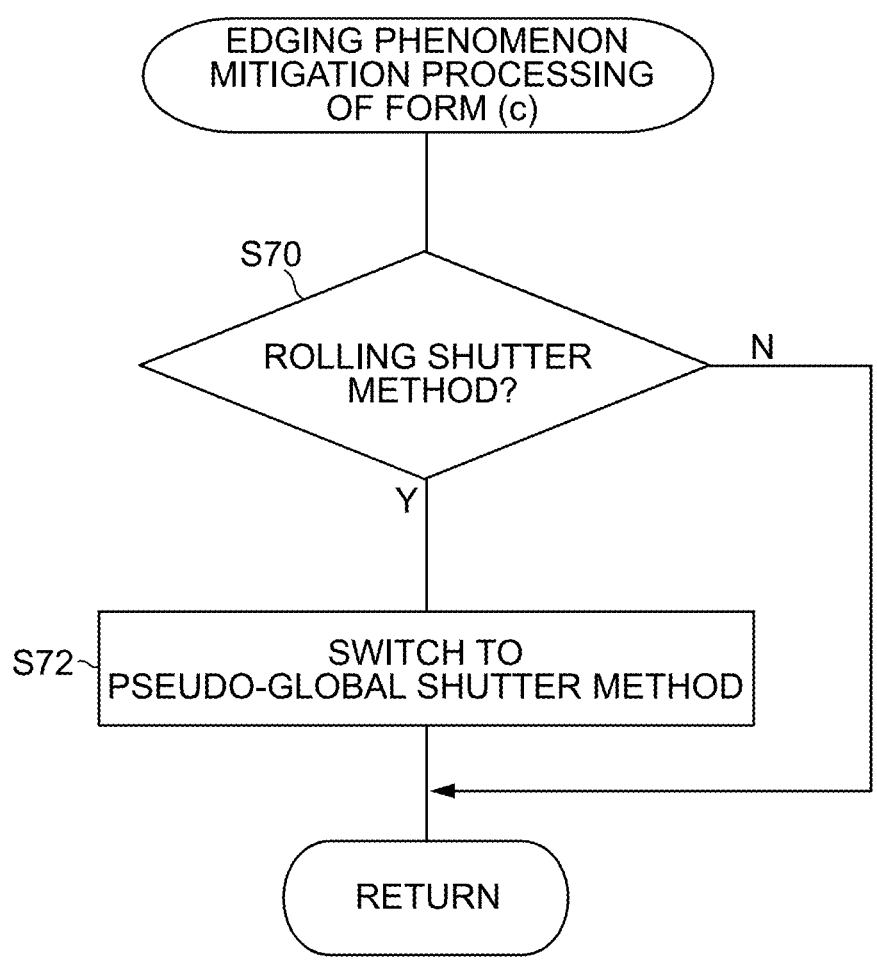
FIG. 20 is a flowchart that illustrates procedures of the edging phenomenon mitigation processing of form (c)

The above described edging phenomenon mitigation processing of form (c), for example, can be performed by the CPU 82 of the processor apparatus 12 shown in FIG. 3, as an exposure control device, instructing the image pickup unit 54 to change the frame rate and the exposure time of the image pickup element 58 through the CPU 80 of the endoscope 11, and also instructing the light source driving circuit 112 to change the driving method or the like of the light source 110 through the CPU 114 of the light source apparatus 13. More specifically, the edging phenomenon mitigation processing of form (c) is executed in the following manner in accordance with the procedures in the flowchart of FIG. 20.

The present edging phenomenon mitigation processing of form (c) is executed in step S14 of FIG. 10 when it is detected that the situation where the edging phenomenon occurs is found by means of the edging phenomenon detection processing in step S10 and the determination processing in step S12 of FIG. 10. First, as the processing in step S70, the CPU 82 determines whether or not the current driving method of the image pickup element 58 is set to the rolling shutter method at a frame rate of 60 p for a time of normal imaging as in FIG. 4.

If the result determined in step S70 is "yes", as the processing in step S72, the CPU 82 switches the driving method of the image pickup element 58 to the pseudo-global shutter method.

That is, the CPU 82 instructs the image pickup unit 54 to switch the driving method of the image pickup element 58 to the rolling shutter method at a frame rate of 30 p and also set the exposure time to the maximum time period (for example, 1/30 sec).

In addition, the CPU 82 instructs the light source driving circuit 112 of the light source apparatus 13 to switch the light source 110 from continuous light emission that causes light to be emitted constantly to intermittent light emission that causes light to be emitted cyclically. A cycle of the intermittent light emission is set to 1/30 sec that matches the frame rate of the image pickup element 58, the periods in which light is emitted in the respective cycles are set so as to be at least a shorter time period than a period in which all lines of the image pickup element 58 are in an exposure state, and the periods in which light is emitted in the respective cycles are synchronized so as to be at a timing within a period in which all lines of the image pickup element 58 are in an exposure state.

As a result, illuminating light that is emitted at a site to be observed from the illuminating windows 41 and 42 of the distal end rigid portion 31 of the endoscope 11 is switched from continuous illumination to intermittent illumination, and the image pickup element 58 is switched to driving by the pseudo-global shutter method at a frame rate of 30 p as shown in FIG. 19.

In contrast, if the result determined in step S70 is "no", since the driving method of the image pickup element 58 is already set to the pseudo-global shutter method, the CPU 82 does not issue an instruction to switch the driving method in the above manner.

Thus, the edging phenomenon mitigation processing of form (c) ends.

Figure 21:
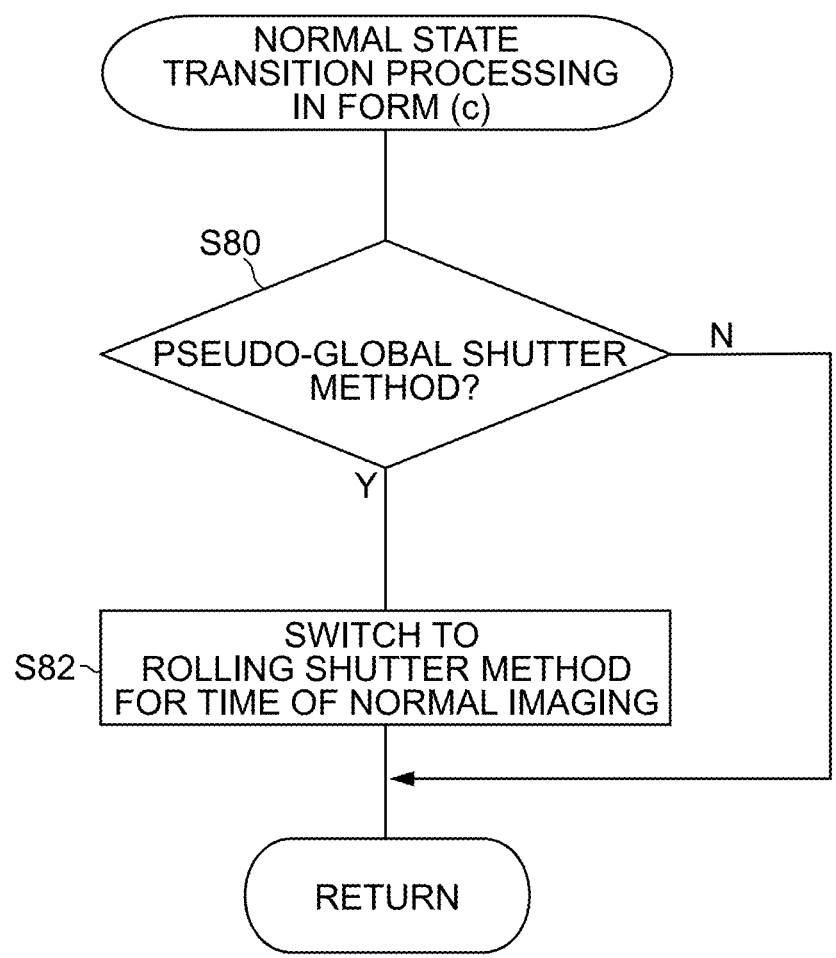
FIG. 21 is a flowchart that illustrates procedures of normal state transition processing in a case where the edging phenomenon mitigation processing of form (c) is adopted.

Next, the normal state transition processing in step S16 in FIG. 10 in a case where the edging phenomenon mitigation processing of form (c) is adopted will be described using the flowchart in FIG. 21.

The normal state transition processing in step S16 of FIG. 10 is executed when it is detected that the situation where the edging phenomenon occurs is not found by means of the edging phenomenon detection processing in step S10 and the determination processing in step S12 of FIG. 10. First, as the processing in step S80, the CPU 82 determines whether or not the current driving method of the image pickup element 58 is set to the pseudo-global shutter method at a frame rate of 30 p as in FIG. 19.

If the result determined in step S80 is "yes", the CPU 82 switches the driving method of the image pickup element 58 to the rolling shutter method for a time of normal imaging.

That is, the CPU 82 instructs the image pickup unit 54 to switch the driving method of the image pickup element 58 to the rolling shutter method at a frame rate of 60 p, and also set the exposure time to a value for a time of normal imaging (for example, ½₀₀ sec).

In addition, the CPU 82 instructs the light source driving circuit 112 of the light source apparatus 13 to switch the light source 110 from intermittent light emission to continuous light emission.

As a result, illuminating light that is emitted at a site to be observed from the illuminating windows 41 and 42 of the distal end rigid portion 31 of the endoscope 11 is switched from intermittent illumination to continuous illumination, and the image pickup element 58 is switched to driving by the rolling shutter method at a frame rate of 60 p for a time of normal imaging as in FIG. 4.

In contrast, if the result determined in step S80 is "no", since the driving method of the image pickup element 58 is already set to the rolling shutter method for a time of normal imaging, the CPU 82 does not issue an instruction to switch the driving method in the above manner.

Thus, the normal state transition processing in a case where the edging phenomenon mitigation processing of form (c) is adopted ends.

FIG. 22A shows droplet images that were imaged in a case where the image pickup element 58 was driven by the pseudo-global shutter method as illustrated in FIG. 19, and FIG. 22B shows droplet images that were imaged in a case where the image pickup element 58 was driven by the rolling shutter method at a time of normal imaging. As shown in FIGS. 22A and 22B, the edging phenomenon is completely suppressed by switching the image pickup element 58 to driving by the pseudo-global shutter method.

Note that a device which switches the illuminating light between continuous illumination and intermittent illumination is not limited to a configuration that switches light emission of the light source 110 of the light source apparatus 13 between continuous light emission and intermittent light emission as described above, and a configuration may also be adopted in which a shutter device that allows or stops the passage of light is disposed in front of the light source 110 that performs continuous light emission, and switching between continuous light emission and intermittent light emission is performed by controlling the shutter device. A different configuration may also be adopted.

Further, the above described form of the pseudo-global shutter method is one example, and the present invention is not limited thereto, and it is sufficient that the exposure control is such that exposure of all scan lines of the same frame is performed simultaneously.

Next, a specific form of the edging phenomenon detection processing in step S10 of the flowchart shown in FIG. 10 will be described.

Any one of the following form (1), form (2), and form (3) can be adopted as a form of edging phenomenon detection processing that detects a situation in which the edging phenomenon occurs.

Form (1) is a form that detects a situation in which the edging phenomenon is actually occurring, and is a form that detects an edge in a horizontal direction of a droplet image within a frame image.

Form (2) is a form that detects a situation in which the edging phenomenon is almost occurring (situation in which the edging phenomenon can occur), and is a form that detects droplet images of droplet that are scattering within a frame image irrespective of the existence or non-existence of an edge in the horizontal direction.

Form (3) is a form that detects a situation in which the edging phenomenon is almost occurring, and is a form that detects that a specific operation whereby it is possible for droplets to be scattered within the range of field of view of the image pickup unit 54 is being performed.

Hereunder, the specific processing contents of forms (1) to (3) are described in order.

First, the edging phenomenon detection processing of form (1) is described.

The edging phenomenon detection processing of form (1) detects an edge in a horizontal direction of a droplet image such as the edges that exist in image regions 180A, 180B, 181A, and 181B in FIG. 23 that is based on FIG. 7. It is thereby possible to directly detect that the edging phenomenon is occurring.

The edging phenomenon detection processing of form (1) can be performed, for example, by the CPU 82 of the processor apparatus 12 shown in FIG. 3 acquiring image data of frame images that were imaged by the image pickup unit 54 from the DSP 86. More specifically, the edging phenomenon detection processing of form (1) can be executed according to the procedures of the flowchart in FIG. 24.

The edging phenomenon detection processing of form (1) is executed in step S10 of FIG. 10. First, as the processing in step S90, the CPU 82 captures image data of frame images that were imaged by the image pickup unit 54 from the DSP 86.

Next, as the processing in step S92, the CPU 82 performs low-pass filter processing regarding the horizontal direction on a frame image captured in step S90 to remove noise within the frame image. This processing is not necessarily required.

Next, as the processing in step S94, the CPU 82 (an edge position candidate detection device included in the CPU 82) detects pixels within the frame image with respect to which a pixel value change amount in the vertical direction is large as candidates for pixels that form an edge in the horizontal direction (edge position candidates). That is, one pixel in the frame image is taken as a pixel of interest, and a difference in the pixel values between the pixel of interest and a pixel at a position above the pixel of interest is determined, and the pixel of interest is taken as a candidate pixel if the difference is greater than or equal to a predetermined threshold value.

Figure 25:
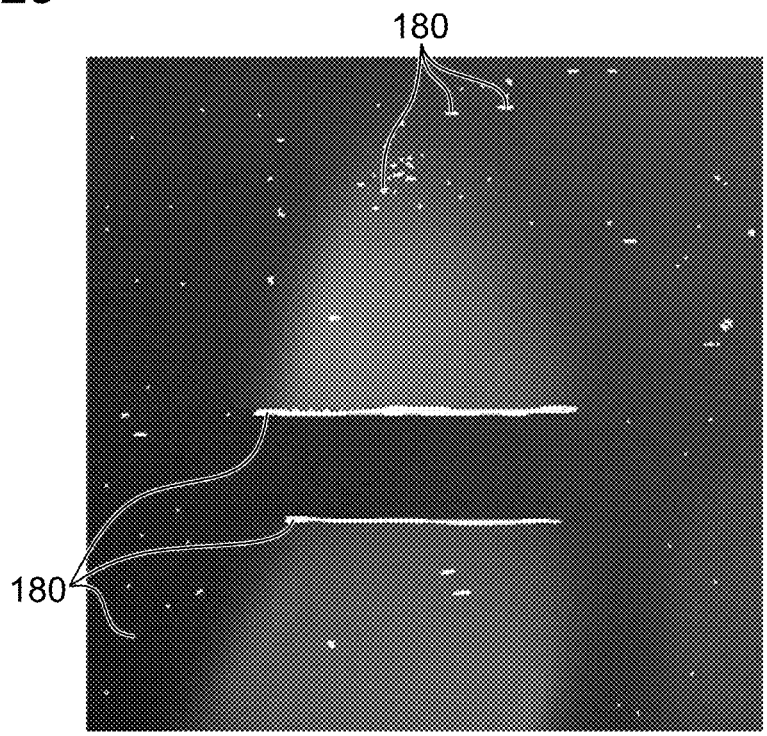
FIG. 25 is an explanatory drawing used to describe the edging phenomenon detection processing of form (1)

The present processing is executed so that all pixels (excluding pixels in the first line) in the frame image are taken in sequence as the pixel of interest to thereby detect all candidate pixels. As a result, for example, candidate pixels 180, 180 . . . that are indicated by dots in FIG. 25 are detected with respect to the droplet image in a region 161 in the portion (B) of FIG. 23. Note that a configuration may also be adopted so as to detect candidate pixels using a luminance value instead of a pixel value.

Figure 26:
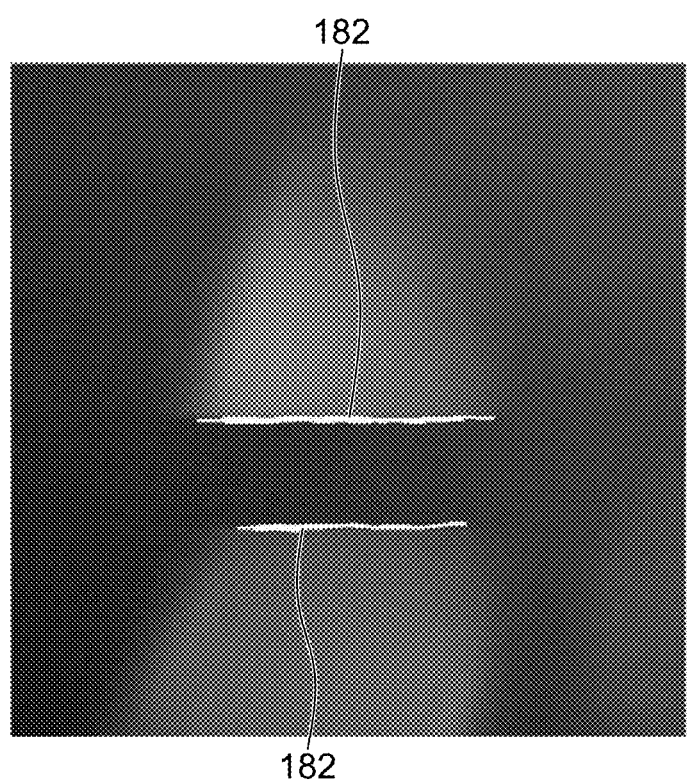
FIG. 26 is an explanatory drawing used to describe the edging phenomenon detection processing of form (1)

Next, as the processing in step S96, among the candidate pixels detected in step S94, the CPU 82 (an edge position detection device included in the CPU 82) detects pixels that are clustered on the same horizontal line as horizontally clustered pixels (edge positions). For example, the candidate pixels are taken in order as a pixel of interest, and a pixel of interest with respect to which a predetermined number or more of candidate pixels are included in a region within a predetermined pixel range in the horizontal direction that is centered on the relevant pixel of interest is detected as a horizontally clustered pixel. As a result, for example, with respect to the candidate pixels detected as shown in FIG. 25, pixels at positions along edges in the horizontal direction of the droplet image are extracted as horizontally clustered pixels 182, 182 . . . as shown in FIG. 26.

By performing the edging phenomenon detection processing of form (1) described above, if a droplet image having an edge in the horizontal direction is present within a frame image, the edge is detected as horizontally clustered pixels.

Figure 27:
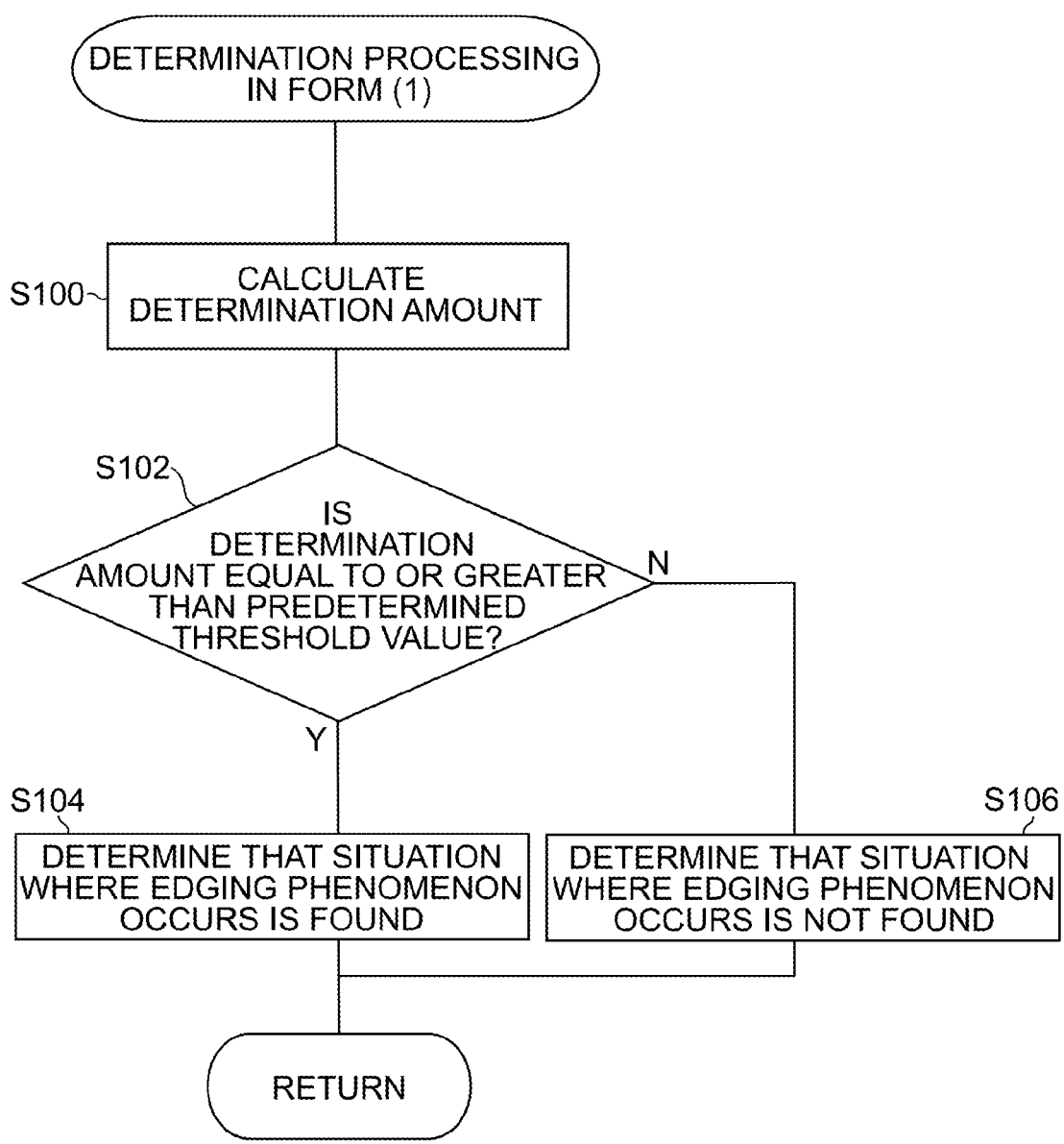
FIG. 27 is a flowchart illustrating procedures of determination processing in step S12 of FIG. 10 in a case where the edging phenomenon detection processing of form (1) is adopted.

Next, determination processing that determines whether or not a situation where the edging phenomenon occurs is found in step S12 of FIG. 10 based on the results of the edging phenomenon detection processing of form (1) described above is described using the flowchart shown in FIG. 27.

As the processing in step S100, the CPU 82 calculates a determination amount for determining whether or not a situation where the edging phenomenon occurs is found using an image feature amount in a frame image that is detected by the above described edging phenomenon detection processing. For example, the number of horizontally clustered pixels detected in the above step S96 is obtained as a determination amount.

Next, as the processing in step S102, the CPU 82 determines whether or not the determination amount is equal to or greater than a predetermined threshold value.

If the result determined in step S102 is "yes", as the processing in step S104, the CPU 82 determines that the situation where the edging phenomenon occurs is found. In this case, the process transitions to the edging phenomenon mitigation processing in step S14 of FIG. 10.

In contrast, if the result determined in step S102 is "no", as the processing in step S106, the CPU 82 determines that the situation where the edging phenomenon occurs is not found. In this case, the process transitions to the normal state transition processing in step S16 in FIG. 10.

The above described edging phenomenon detection processing of form (1) can be used in a case where any of the aforementioned forms (a) to (c) are adopted as the edging phenomenon mitigation processing.

In a case where the edging phenomenon mitigation processing of form (a) is adopted, information of the image region of the horizontally clustered pixels detected by step S96 is referred to in the edging phenomenon mitigation processing as information that shows an image region of an edge in the horizontal direction of a droplet image, and an image region on which to execute blurring processing can be decided based thereon.

Note that, in the edging phenomenon mitigation processing of form (a), an image region including an edge periphery, an image region of an entire droplet image or the like, and not just an image region of an edge, may be taken as an image region on which to execute blurring processing, and the image region on which to execute blurring processing may be determined in the present edging phenomenon detection processing of form (1) and referred to in the edging phenomenon mitigation processing.

In addition, the aforementioned determination amount may also be a length in the horizontal direction of an edge that is based on the horizontally clustered pixels detected in step S96, or may also be the number of edges.

It is also possible to perform the edging phenomenon detection processing of form (1) at the DSP 86 or another image processing unit in accordance with an instruction from the CPU 82, and not at the CPU 82.

Next, the edging phenomenon detection processing of form (2) will be described.

The edging phenomenon detection processing of form (2) detects droplet images of scattering droplets within a frame image. It is thereby possible to detect that the edging phenomenon is almost occurring.

Since a droplet image of a scattering droplet is an image in which a droplet traverses the range of field of view of the image pickup unit 54 at high speed, there are many cases in which the droplet only appears in a frame image for a single frame. Further, when the edging phenomenon is occurring, since one part of the droplet does not appear in the frame image, even if the droplet appears over two or more frames, there is a low possibility of the shape of the droplet being the same in each frame.

On the other hand, if an image is one of an object other than droplets that are being scattered, it is difficult to consider that the image will be of an object that is moving at a high speed, and hence the object will appear as an image with the same pattern in frame images of two frames that are temporally adjacent.

Accordingly, it can be determined that an object for which an image of the same pattern does not appear in frame images of two temporally adjacent frames is a scattering droplet.

Conversely, it can be determined that an object for which an image of the same pattern appears in frame images of two temporally adjacent frames is not a scattering droplet.

Figure 28:
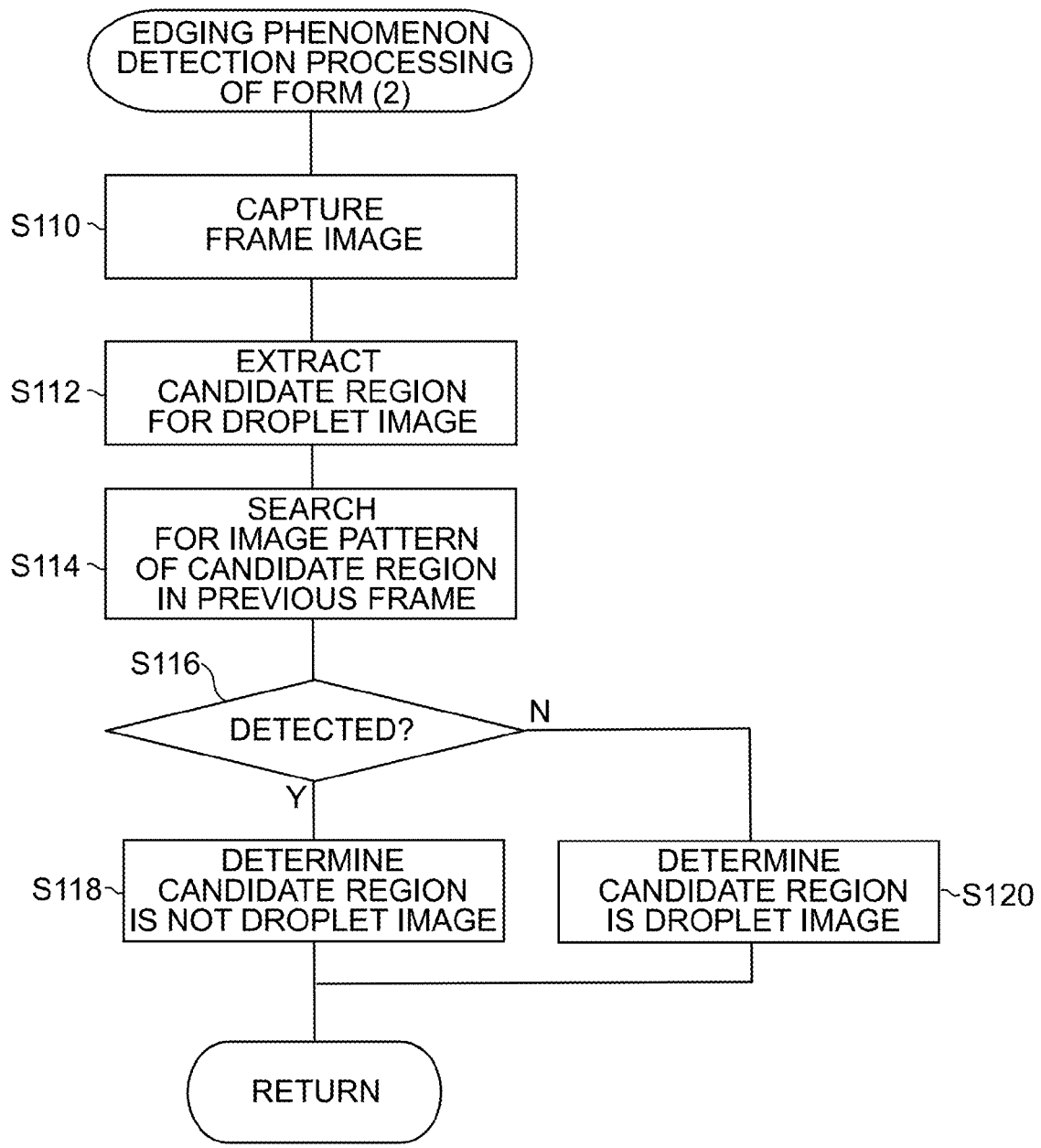
FIG. 28 is a flowchart illustrating an outline of procedures of edging phenomenon detection processing of form (2)

The edging phenomenon detection processing of form (2) can be performed, for example, by the CPU 82 of the processor apparatus 12 shown in FIG. 3 acquiring image data of frame images that were imaged by the image pickup unit 54 from the DSP 86. More specifically, the edging phenomenon detection processing of form (2) can be executed in the following manner in accordance with the procedures in the flowchart of FIG. 28.

The edging phenomenon detection processing of form (2) is executed in step S10 of FIG. 10. First, as the processing in step S110, the CPU 82 captures image data of frame images that were imaged by the image pickup unit 54 from the DSP 86.

Next, as the processing in step S112, the CPU 82 (a pattern matching determination device included in the CPU 82) takes a frame image captured by step S110 as the frame image of a frame of interest (frame image of interest), and extracts an image region that can be regarded as a single object from the frame image of interest as a candidate region for a droplet image. The image region that can be regarded as a single object can be determined, for example, based on luminance or continuity of a color.

Figure 29B:
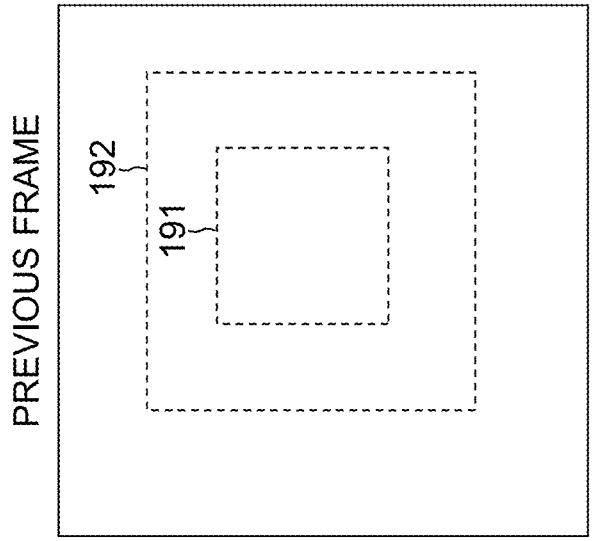
FIGS. 29A and 29B are explanatory drawings used to describe the edging phenomenon detection processing of form (2)
Figure 29A:
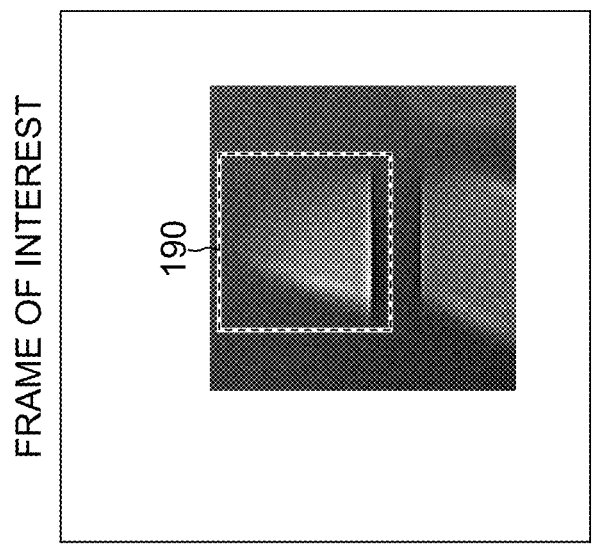

As a result, for example, an image region 190 shown in FIG. 29A is extracted as a candidate region.

Next, as the processing in step S114, the CPU 82 (pattern matching determination device) performs pattern matching processing to search a frame image that is one frame prior to the frame image of interest for an image region that matches the image pattern of the candidate region that was extracted from the frame image of interest. If a plurality of candidate regions were extracted in step S112, the CPU 82 searches for image regions that match the image patterns with respect to the respective candidate regions.

Note that, it is sufficient to search for an image pattern of a candidate region within a frame image of a temporally adjacent frame (adjacent frame image) with respect to the frame of interest, and a configuration may also be adopted in which an image pattern of a candidate region is searched for within a frame image that is one frame after the frame of interest, and not within a frame image that is one frame before the frame of interest.

Further, a search area in a frame image of the previous frame when searching for an image pattern of a candidate region need not be the area of the entire screen of the frame image, and may be an image region at the same position as the candidate region on the screen as well as an image region that is limited to the surrounding area thereof as shown in FIG. 29B. For example, a search area with respect to the candidate region 190 in FIG. 29A can be an image region 191 in FIG. 29B that is at the same position and is the same area on the screen as the candidate region 190 as well as an image region 192 that includes a portion surrounding the image region 191. However, the entire screen of the frame image may also be taken as the search area.

Next, as the processing in step S116, the CPU 82 (pattern matching determination device) determines whether or not an image pattern of the candidate region is detected in the frame image of the previous frame.

If the result determined in step S116 is "yes", as the processing in step S118, the CPU 82 determines that the image of the candidate region is not an image of a scattering droplet.

In contrast, if the result determined in step S116 is "no", as the processing in step S120, the CPU 82 determines that the image of the candidate region is an image of a scattering droplet.

A droplet image of a scattering droplet is detected by means of the above-described edging phenomenon detection processing of form (2).

Note that, in the processing for pattern matching, for example, while an image region of an image to be compared with an image of a comparison region is being moved within an adjacent frame image, the degrees of difference between the compared images are sequentially determined. An image of an image region in the adjacent frame image at a time when the degree of difference is the lowest is taken as the image that is most similar to the image pattern of the candidate region, and if the minimum value of the degree of difference is equal to or greater than a predetermined threshold value, it is desirable to determine that the image pattern of the candidate region was not found in the adjacent frame image (determine that the image is an image of a scattering droplet). The degree of difference can be set as, for example, the sum total of absolute values of differences between pixel values of corresponding pixels of the two images that are compared.

Next, determination processing that determines whether or not a situation where the edging phenomenon occurs is found in step S12 of FIG. 10 based on results of the above described edging phenomenon detection processing of form (2) will be described. Since the present processing is performed in a similar manner to the determination processing in a case where the edging phenomenon detection processing of form (1) is adopted, the present processing will be described using the flowchart in FIG. 27 that is used at the time of the edging phenomenon detection processing of form (1).

As the processing in step S100, the CPU 82 calculates a determination amount for determining whether or not a situation where the edging phenomenon occurs is found using an image feature amount in a frame image that is detected by the above described edging phenomenon detection processing. For example, the number of candidate regions that were determined as being droplet images in the above described step S120 is obtained as the determination amount.

Next, as the processing in step S102, the CPU 82 determines whether or not the determination amount is equal to or greater than a predetermined threshold value.

If the result determined in step S102 is "yes", as the processing in step S104, the CPU 82 determines that the situation where the edging phenomenon occurs is found. In this case, the process transitions to the edging phenomenon mitigation processing in step S14 of FIG. 10.

In contrast, if the result determined in step S102 is "no", as the processing in step S106, the CPU 82 determines that the situation where the edging phenomenon occurs is not found. In this case, the process transitions to the normal state transition processing in step S16 in FIG. 10.

Note that the sum total of areas of candidate regions that were determined as being droplet images can also be taken as a determination amount.

The above described edging phenomenon detection processing of form (2) can also be used in a case where any of the aforementioned forms (a) to (c) are adopted as the edging phenomenon mitigation processing.

In a case where the edging phenomenon mitigation processing of form (a) is adopted, information of the image region in which a droplet image of a scattering droplet was detected as described above is referred to in the edging phenomenon mitigation processing, and an image region on which to execute blurring processing can be decided based thereon. In the edging phenomenon mitigation processing of form (a), in a case where an image region of only an edge in the horizontal direction or an image region of an edge periphery portion is taken as an image region on which to execute blurring processing, for example, it is sufficient to execute processing that detects an edge as in the edging phenomenon detection processing of form (1), and a configuration may be adopted so that such processing is performed in the present edging phenomenon detection processing of form (2) and can be referred to in the edging phenomenon mitigation processing, or such processing may be executed in the edging phenomenon mitigation processing.

Further, the edging phenomenon detection processing of form (2) can be used in combination with the edging phenomenon detection processing of form (1). For example, a configuration can be adopted that performs edging phenomenon mitigation processing only in a case where it is detected by the edging phenomenon detection processing of both form (1) and form (2) that a situation where the edging phenomenon occurs is found.

In addition, it is possible to perform the edging phenomenon detection processing of form (2) at the DSP 86 or another image processing unit in accordance with an instruction from the CPU 82, and not at the CPU 82.

Next, the edging phenomenon detection processing of form (3) will be described.

The edging phenomenon detection processing of form (3) detects that a specific operation is being performed that can cause droplets to scatter within the range of field of view of the image pickup unit 54. As a result, the fact that the edging phenomenon is almost occurring can be detected.

The edging phenomenon detection processing of form (3) can be performed, for example, by the CPU 82 of the processor apparatus 12 that is shown in FIG. 3 detecting an operational state of an operation member that performs an operation that can cause droplets to scatter within the range of field of view of the image pickup unit 54. Specifically, the edging phenomenon detection processing of form (3) is executed as described below.

The CPU 82 is configured so that a status signal indicating an operational state of the air/water feeding button 22 of the operation portion 15 for spraying air (gas) or water from the air/water feeding nozzle 43 at the distal end of the insertion portion 14 of the endoscope 11 and a status signal indicating an operational state of the suction button 23 of the operation portion 15 for performing suction of body fluid and the like from the forceps outlet 20 are provided thereto.

Furthermore, in the case of using an apparatus for spraying water that washes a site to be observed or a liquid such as a dye that dyes the site to be observed a predetermined color by utilizing a predetermined channel such as the forceps channel at the site to be observed, a status signal indicating an operational state of a switch (a foot switch or the like) for spraying a liquid in the apparatus is provided to the CPU 82.

In the edging phenomenon detection processing in step S10 of FIG. 10, the CPU 82 detects the operational state of the aforementioned operation members based on the status signals. If it is detected as a result that any of the operation members is in an operational state in which the operation member is spraying a liquid or a gas (feeding a fluid), it is taken that the CPU 82 detected that an operation that can cause droplets to scatter within the range of field of view of the image pickup unit 54 is being performed.

In contrast, if none of the operation members is in an operational state in which feeding of a fluid or suction is performed, it is taken that the CPU 82 did not detect that an operation that can cause droplets to scatter within the range of field of view of the image pickup unit 54 is being performed.

Next, determination processing that determines whether or not the situation where the edging phenomenon occurs is found in step S12 of FIG. 10 will be described. In a case where, by performing the above described edging phenomenon detection processing, the CPU 82 detected that an operation that can cause droplets to scatter within the range of field of view of the image pickup unit 54 is being performed, the CPU 82 determines that the situation where the edging phenomenon occurs is found, and transitions to the edging phenomenon mitigation processing in step S14 of FIG. 10.

In contrast, in a case where, by performing the above described edging phenomenon detection processing, the CPU 82 did not detect that an operation that can cause droplets to scatter within the range of field of view of the image pickup unit 54 is being performed, the CPU 82 determines that the situation where the edging phenomenon occurs is not found, and transitions to the normal state transition processing in step S16 of FIG. 10.

Note that, an operation that is taken as a target when detecting if an operation that can cause droplets to scatter within the range of field of view of the image pickup unit 54 is being performed may be any one operation or a plurality of operations among the above described operations, and an operation that performs feeding of a gas or an operation that performs suction of a fluid may also be excluded from the target operations.

The above described edging phenomenon detection processing of form (3) can be used when adopting the aforementioned form (b) and form (c) as edging phenomenon mitigation processing.

In addition, the edging phenomenon detection processing of form (3) can be used in combination with the edging phenomenon detection processing of form (1) or form (2). For example, a configuration can be adopted that performs edging phenomenon mitigation processing only in a case where it is detected by at least the edging phenomenon detection processing of form (3) that a situation where the edging phenomenon occurs is found.

Next, erroneous detection prevention processing for preventing erroneous detection in a case where form (1) or form (2) is adopted as the edging phenomenon detection processing is described.

First, erroneous detection prevention processing of forms (X-1) to (X-4) that prevent an image other than a droplet image being erroneously detected at a droplet image are described in order.

First, erroneous detection prevention processing of form (X-1) will be described. The erroneous detection prevention processing of form (X-1) is applicable to a case in which the edging phenomenon detection processing of form (1) is adopted. In a case where an object image other than a droplet image has an edge in the horizontal direction, the erroneous detection prevention processing of form (X-1) prevents the edge from being erroneously detected as the edge of a droplet image.

For example, in some cases an image of an artifact such as a distal end hood appears in an image that was picked up by the image pickup unit 54 as shown in FIG. 31, and there is a possibility that edges that can be regarded as being in the horizontal direction exist in the image of the artifact, as in the case of a region 200 in the portion (A) of FIG. 31. In this case, in the edging phenomenon detection processing of form (1), the edges in the horizontal direction of the image of the artifact are erroneously detected as edges of a droplet image.

On the other hand, although the position or shape of a droplet image appearing in each frame image of two temporally adjacent frames changes between the frame images, an image of an artifact hardly changes at all between the frame images.

Therefore, it is possible to prevent the aforementioned erroneous detection by executing the following processing after detecting an edge in the horizontal direction in the edging phenomenon detection processing of form (1) as horizontally clustered pixels.

In the edging phenomenon detection processing of form (1), if an edge in the horizontal direction was detected in the frame image of the current frame, the CPU 82 (a differential image generation device included in the CPU 82) determines a difference between the frame image of the current frame and a frame image of the frame immediately before the current frame with respect to an image region around the detected edge, and generates a differential image.

Note that it is sufficient to obtain a differential image between the frame image of the current frame and a frame image of an adjacent frame that is temporally adjacent to the current frame, and a differential image between the frame image of the current frame and a frame image of the frame after the current frame (not the frame before the current frame) may be obtained.

It is assumed that the differential image shows an image in which the pixel values of the respective pixels are values that are obtained by subtracting the pixel values of pixels at corresponding positions of the adjacent frame image from the pixel values of the respective pixels of the frame image of the current frame. However, the differential image may be an image determined by another method as long as the differential image is an image showing a difference between the frame image of the current frame and the frame image of an adjacent frame.

In a case where, as shown in the portion (A) of FIG. 30, an edge detected in the frame image of the current frame is the edge of a droplet image, the droplet image in the frame image of the previous frame differs as shown in the portion (B) of FIG. 30, and an image of the edge in the frame image of the current frame remains in the differential image as shown in the portion (C) of FIG. 30.

Accordingly, in a case where an image of an edge that was detected by edging phenomenon detection processing in this manner also exists in the differential image (a case where pixel values of the image of the edge are equal to or greater than a predetermined threshold value in the differential image), the CPU 82 (a differential image edge position determination device included in the CPU 82) determines that the edge was detected appropriately and is not an erroneously detected edge.

On the other hand, in a case where, as shown in the portion (A) of FIG. 31, an edge detected in the frame image of the current frame is an edge of an image of an artifact and not an edge of a droplet image (a case where pixel values of the image of the edge are less than the aforementioned threshold value in the differential image), as shown in the portion (B) of FIG. 31, the image of the artifact in the frame image of the previous frame approximately matches the image in the frame image of the current frame, and an image of the edge in the frame image of the current frame does not remain in the differential image as shown in the portion (C) of FIG. 31.

Accordingly, when an image of an edge that was detected by edging phenomenon detection processing in this manner does not exist in a differential image, the CPU 82 (a differential image edge position determination device) determines that the edge was detected erroneously. Therefore, the CPU 82 excludes the edge from the detection results of the edging phenomenon detection processing.

Note that the specific form of form (X-1) described above is such that, after detecting an edge in a horizontal direction as horizontally clustered pixels in the edging phenomenon detection processing of form (1), a differential image between a frame image of the current frame and a frame image of an adjacent frame is obtained with respect to an image region around the detected edge, and it is determined whether or not the edge belongs to a droplet image based on the existence or non-existence of an image of the edge in the differential image (whether or not pixel values of the image of the edge are equal to or greater than a predetermined threshold value). However, form (X-1) is not limited thereto.

For example, a configuration may also be adopted such that, before executing the edging phenomenon detection processing of form (1), a differential image between a frame image of the current frame and a frame image of an adjacent frame with respect to the entire image region of the frame image is generated by the CPU 82 (a differential image generation device included in the CPU 82), an image of a fixed object such as an artifact is excluded therefrom to extract only a droplet image, and the edging phenomenon detection processing of form (1) is then executed with respect to the resulting differential image.

Figure 24:
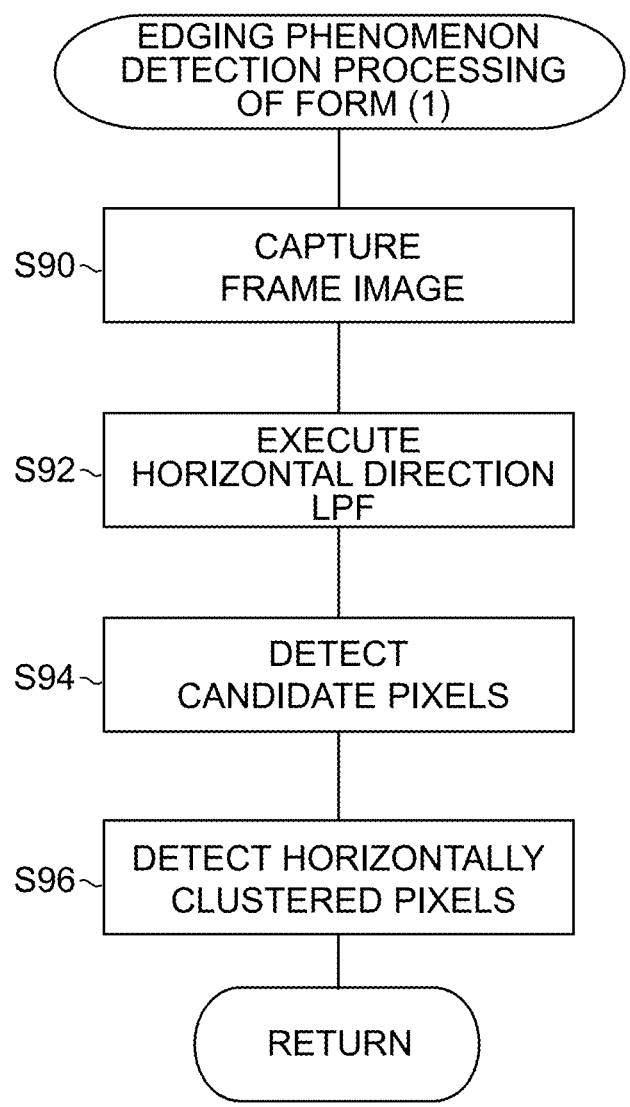
FIG. 24 is a flowchart illustrating an outline of procedures of the edging phenomenon detection processing of form (1)

That is, in step S92 to step S96 in the flowchart of FIG. 24 that shows procedures of the edging phenomenon detection processing of form (1), an image that is the object of processing may be a differential image showing a difference between the current frame and an adjacent frame, and not the frame image of the current frame.

Next, erroneous detection prevention processing of form (X-2) will be described. The erroneous detection prevention processing of form (X-2) can be applied to a case where the edging phenomenon detection processing of form (1) or form (2) is adopted. In a situation in which the edging phenomenon cannot occur, such as a case where the insertion portion 14 (image pickup unit 54) of the endoscope 11 is not inserted into a body cavity of a patient before the start of an examination or after the end of an examination, the erroneous detection prevention processing of form (X-2) prevents an erroneous detection to the effect that the situation where the edging phenomenon occurs is found by the edging phenomenon detection processing in step S10 and the determination processing in step S12 of FIG. 10.

In a situation where the image pickup unit 54 is not inserted into a body cavity of a patient, an artifact such as a fluorescent light on a ceiling is reflected in an image that was imaged with the image pickup unit 54, and if the image of the fluorescent light or the like has an edge in the horizontal direction, it is possible that a situation will arise in which the edge is erroneously detected as a droplet image.

On the other hand, in a situation where the image pickup unit 54 is not inserted into a body cavity of a patient, a situation cannot occur in which droplets are scattered as the result of air/water feeding or the like, and such a situation where the edging phenomenon occurs is not found. Consequently, in such a situation, if it was detected that the situation where the edging phenomenon occurs is found by edging phenomenon detection processing and determination processing, the detection is erroneous even in a case where either of form (1) and form (2) was adopted as the edging phenomenon detection processing.

Further, in some cases the processor apparatus 12 or the light source apparatus 13 has a light amount control function that controls the amount of illuminating light in accordance with the brightness of a frame image that was imaged by the image pickup unit 54. In this case, because reflected light at a droplet is reflected brightly in an image, in a situation in which the edging phenomenon occurs, that is, a situation in which droplets are scattering close to the observation window 40, the amount of the illuminating light is restricted (reduced). Accordingly, in a case where the amount of illuminating light is the maximum light amount, the situation where the edging phenomenon is not occurring is found, and in a case where it was detected that the situation where the edging phenomenon occurs is found by means of the edging phenomenon detection processing and determination processing, the detection is erroneous even in a case where either of form (1) and form (2) was adopted as the edging phenomenon detection processing.

Therefore, the above described kind of erroneous detection can be prevented by executing the following processing.

First, before executing the edging phenomenon detection processing in step S10 of FIG. 10, the CPU 82 (a light amount determination device included in the CPU 82) determines whether or not illuminating light is being supplied from the light source apparatus 13 to the endoscope 11, that is, whether the light source 110 is on or off (whether or not the amount of illuminating light is 0).

If it is determined that the light source 110 is off, since the situation where the image pickup unit 54 is not inserted into a body cavity is found, the CPU 82 does not execute the edging phenomenon detection processing in step S10 of FIG. 10, and determines in the determination processing in step S12 that the situation where the edging phenomenon occurs is not found.

In contrast, if it is determined that the light source 110 is on, the CPU 82 determines whether or not the amount of illuminating light being emitted from the light source 110 is the maximum light amount. If it is determined that the amount of illuminating light is the maximum light amount, since the situation where the edging phenomenon is not occurring is found, the CPU 82 does not execute the edging phenomenon detection processing in step S10 of FIG. 10, and determines in the determination processing in step S12 that the situation where the edging phenomenon occurs is not found.

According to the above described processing, the edging phenomenon detection processing is not executed in a case where the light source 110 is off or a case where the amount of illuminating light is the maximum light amount, and in other cases the edging phenomenon detection processing is executed. Thus, in a situation in which the edging phenomenon cannot occur, an erroneous detection to the effect that the situation where the edging phenomenon occurs is found is prevented.

Note that a configuration may also be adopted such that, instead of not executing the edging phenomenon detection processing in a case where the amount of illuminating light is the maximum light amount, the edging phenomenon detection processing is not executed if the amount of illuminating light is a light amount that is equal to or greater than a predetermined threshold value. Further, a configuration may be adopted such that the edging phenomenon detection processing is not executed if the amount of illuminating light is not within a predetermined range.

Next, erroneous detection prevention processing of form (X-3) will be described. The erroneous detection prevention processing of form (X-3) can be applied to a case where the edging phenomenon detection processing of form (1) or form (2) is adopted. In a situation in which there is a low possibility of the edging phenomenon occurring, such as a case where the image pickup unit 54 is brought close to an object of a site to be observed and is performing imaging, the erroneous detection prevention processing of form (X-3) prevents an erroneous detection by making it difficult for the edging phenomenon detection processing in step S10 and the determination processing in step S12 of FIG. 10 to detect that the situation where the edging phenomenon occurs is found.

In a case where the image pickup unit 54 (the observation window 40) is brought close to an object of a site to be observed and is performing imaging, basically few air/water feeding or the like is performed and the possibility of the edging phenomenon occurring is low. It is considered that the closer the image pickup unit 54 is to the site to be observed, the lower the possibility is that the edging phenomenon will occur.

In addition, in a case where the image pickup unit 54 has a zoom optical device that can change a focal distance of the objective optical system 50 to change a zoom magnification ratio of an optical zoom, air/water feeding or the like is seldom performed when the zoom magnification ratio is increased and imaging is being performed, and thus the possibility of the edging phenomenon occurring is low. That is, it is considered that the larger that the zoom magnification ratio (focal distance) of the optical zoom of the image pickup unit 54 is, the lower the possibility that the edging phenomenon will occur.

Figure 32:
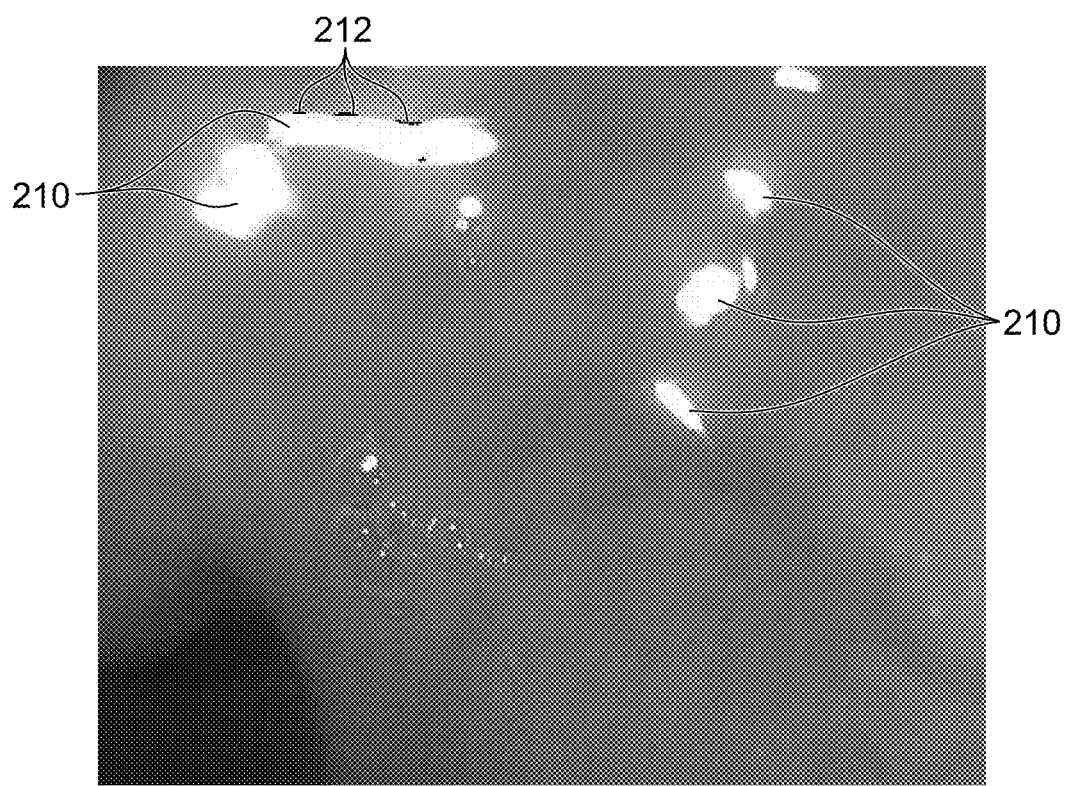
FIG. 32 is an explanatory drawing used to describe erroneous detection prevention processing of form (X-3)

In addition, in a case where the image pickup unit 54 is brought close to an object of a site to be observed and is performing imaging, or in a case where the zoom magnification ratio of the optical zoom in the image pickup unit 54 is large, as shown in FIG. 32, halation (a high luminance region) 210 of a large area arises in a frame image that is imaged by the image pickup unit 54. The area of halation in the frame image increases in accordance with the proximity of the image pickup unit 54 to the object of the site to be observed, or as the zoom magnification ratio of the optical zoom increases. In some cases, edges in the horizontal direction that are designated by reference numeral 212 in FIG. 32 arise in the halation, and it is possible for such edges to be erroneously detected as an edge of a droplet image.

Therefore, by executing the following processing, it is possible to prevent erroneous detection in a situation in which there is a low possibility of the edging phenomenon occurring.

When executing the edging phenomenon detection processing in step S10 of FIG. 10 by form (1) or form (2), the CPU 82 (a high luminance region extraction device included in the CPU 82) detects a halation region that arises in the frame image. That is, the CPU 82 detects (extracts) a pixel region (high luminance region) of pixels having a high luminance that is equal to or greater than a predetermined threshold value.

The larger that the area of the region of halation is, the closer that the CPU 82 determines the image pickup unit 54 is to the object of the site to be observed, and the larger the CPU 82 makes the threshold value with respect to the determination amount to be used in the determination processing in step S12 of FIG. 10.

In this case, the term "determination amount" refers to a value for determining whether or not the situation where the edging phenomenon occurs is found. In the edging phenomenon detection processing of form (1), for example, as described in the foregoing, the determination amount shows a number of pixels of the horizontally clustered pixels that were detected in step S96 of FIG. 24.

In the edging phenomenon detection processing of form (2), for example, the determination amount shows a number of candidate regions that were determined as being a droplet image of a scattering droplet or shows a sum total of the areas thereof as described above.

In the determination processing in step S12 of FIG. 10, if the determination amount is equal to or greater than the predetermined threshold value it is determined that the situation where the edging phenomenon occurs is found, while if the determination amount is less than the threshold value it is determined that the situation where the edging phenomenon occurs is not found.

Therefore, by increasing the threshold value as the size of the area of the halation region increases, the closer the image pickup unit 54 is to the object of the site to be observed, or the larger that the zoom magnification ratio of the optical zoom of the image pickup unit 54 is, that is, the lower the possibility of the edging phenomenon occurring becomes, the stricter that the condition for determining that the situation where the edging phenomenon occurs is found can be made in the determination processing in step S12, and the more difficult it can be made to determine that the situation where the edging phenomenon occurs is found.

Note that an area of the region of halation may be taken as the sum total of all regions of halation that have arisen on a frame image, or may be taken as a maximum value among the areas of respective halation regions that arise at separate places.

Further, a configuration may be adopted such that, in a case where the area of a halation region is equal to or greater than the predetermined threshold value, the edging phenomenon detection processing in step S10 is not performed and it is determined in the determination processing in step S12 that the situation where the edging phenomenon occurs is not found.

In addition, in the edging phenomenon detection processing of form (1) or form (2), only regions of halation (high luminance regions larger than a predetermined luminance value) can be excluded from a target region for detection of an edge or a droplet image. Further, a configuration may also be adopted in which the CPU 82 (a high luminance region determination device included in the CPU 82) determines whether or not an area of such a high luminance region is equal to or greater than a predetermined threshold value, and a high luminance region that was determined as being equal to or greater than the predetermined threshold value is excluded from a target region for detection of an edge or a droplet image.

Further, in a case where it is possible for the image pickup unit 54 to change the zoom magnification ratio (focal distance) of the optical zoom, a configuration may be adopted such that the image pickup unit 54 acquires information of the zoom magnification ratio (focal distance) from the CPU 82 and changes the threshold value with respect to the determination amount that is used in the determination processing in step S12 of FIG. 10 in accordance with the optical zoom usage situation, or changes the relevant threshold value in the case of excluding a high luminance region of an area that is greater than or equal to a predetermined threshold value from a target region for detection of an edge or a droplet image. That is, a configuration may be adopted so as to increase the threshold value as the zoom magnification ratio increases.

Next, the erroneous detection prevention processing of form (X-4) will be described. The erroneous detection prevention processing of form (X-4) can be applied to a case where the edging phenomenon detection processing of form (1) or form (2) is adopted. In a case where images which could be detected as an edge in the horizontal direction of a droplet image or as a droplet image arise by chance, the erroneous detection prevention processing of form (X-4) prevents those images being erroneously detected as an edge in the horizontal direction of a droplet image or as a droplet image.

The above described erroneous detection can be prevented by executing the following processing.

The CPU 82 stores a degree of occurrence of edges or droplet images in a frame image that are detected when the edging phenomenon detection processing of form (1) or form (2) was executed in step S10 of FIG. 10.

For example, a determination amount obtained by the edging phenomenon detection processing of form (1) or form (2) or an image feature amount that can be taken as a determination amount can be used as a value showing the degree of occurrence. For example, in the edging phenomenon detection processing of form (1), the number of pixels of the horizontally clustered pixels that were detected in step S96 of FIG. 24, a number of edges based on the horizontally clustered pixels (number of droplet images having an edge), or the sum total of the lengths of the edges or the like can be taken as a value that shows the degree of occurrence.

In the edging phenomenon detection processing of form (2), for example, the number of candidate regions that were determined as being a droplet image of a scattering droplet as described above or a sum total of the areas of the candidate regions can be taken as a value that shows the degree of occurrence.

When detecting edges or droplet images with respect to a new frame image, the CPU 82 (an image region occurrence degree determination device included in the CPU 82) determines a temporal average value of the degrees of occurrence of edges or droplet images within a predetermined time period immediately prior thereto, and if that average value is less than or equal to a predetermined threshold value, the CPU 82 determines in the determination processing in step S12 of FIG. 10 that the situation where the edging phenomenon occurs is not found.

Thus, even in a case where images which could be detected as an edge in the horizontal direction of a droplet image or as a droplet image arise by chance, erroneous detection of those images as an edge in the horizontal direction of a droplet image or as a droplet image is prevented.

Next, as erroneous detection prevention processing of form (Y), erroneous detection prevention processing will be described with respect to a case where the edging phenomenon detection processing of form (1) or form (2) is adopted and the edging phenomenon mitigation processing of form (b) is adopted.

The erroneous detection prevention processing of form (Y) prevents erroneous detection which occurs due to appropriate detection of a situation in which the edging phenomenon occurs not being possible in the edging phenomenon detection processing of form (1) or form (2) due to execution of the edging phenomenon mitigation processing of form (b).

When the edging phenomenon mitigation processing of form (b) is executed, since occurrence of the edging phenomenon is mitigated by lengthening the exposure time of the image pickup element 58, even in a situation in which droplets are scattering, it is difficult to detect that the situation where the edging phenomenon occurs is found.

Therefore, even in a case in which it would be determined that the situation where the edging phenomenon occurs is found in the determination processing in step S12 of FIG. 10 if the exposure time were the time period for a time of normal imaging, when the exposure time is longer than at a time of normal imaging, there is a possibility that it will be determined that the situation where the edging phenomenon occurs is not found.

When such a situation arises, processing that returns the exposure time to that for a time of normal imaging or processing that shortens the exposure time is performed by the normal state transition processing in step S16 of FIG. 10.

Subsequently, when the edging phenomenon detection processing is executed, it is determined that the situation where the edging phenomenon occurs is found, and processing is performed to lengthen the exposure time once more.

While a situation in which droplets are scattering in this manner is continuing, unnecessary changes in the exposure time are repeated.

Therefore, by executing the following processing, erroneous detection of the existence or non-existence of occurrence of the edging phenomenon as described above is prevented, and this is suitable for preventing unnecessary changes in the exposure time.

In the determination processing in step S12 after execution of the edging phenomenon detection processing of form (1) or form (2) in step S10 of FIG. 10, the CPU 82 uses a determination amount in a similar manner to the erroneous detection prevention processing of form (X-3).

Figure 33:
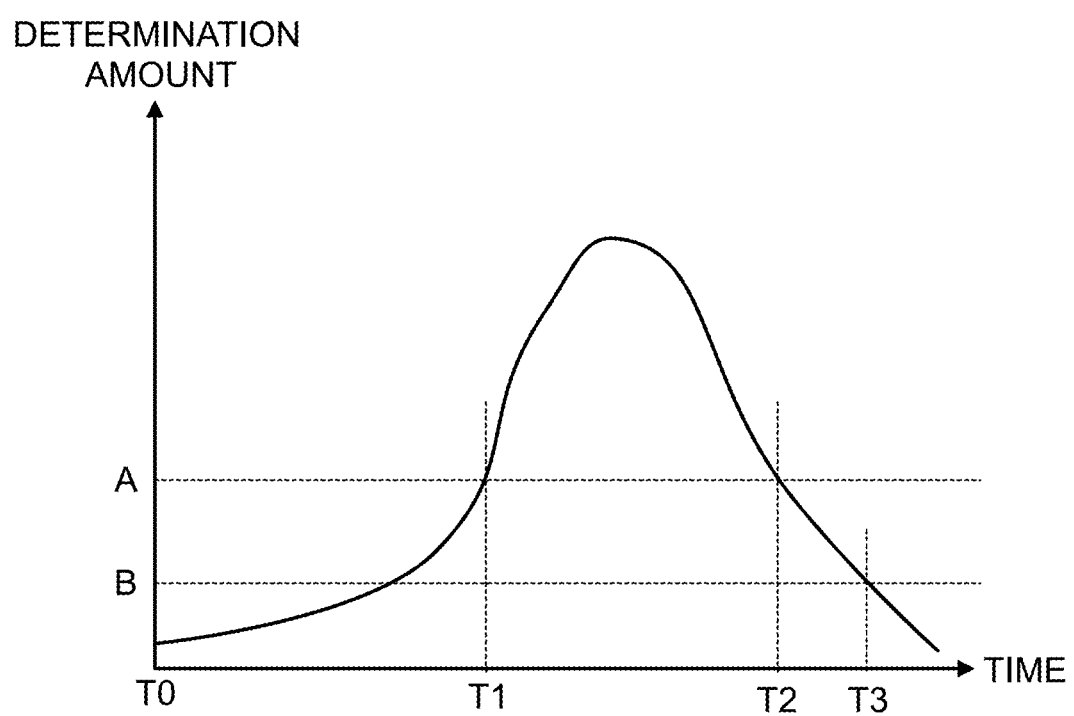
FIG. 33 is a view used to describe erroneous detection prevention processing of form (Y).

If it was determined in the previous determination processing in step S12 that the situation where the edging phenomenon occurs is not found, a threshold value with respect to the determination amount is set to, for example, a value A (first threshold value) as shown in FIG. 33.

Further, in the current determination processing, if the determination amount is equal to or greater than the threshold value A, it is determined that the situation where the edging phenomenon occurs is found, while if the determination amount is less than the threshold value A, it is determined that the situation where the edging phenomenon occurs is not found.

In contrast, if it was determined in the previous determination processing in step S12 that the situation where the edging phenomenon occurs is found, a threshold value with respect to the determination amount is set to, for example, a value B (second threshold value) that is less than the value A as shown in FIG. 33.

Further, in the current determination processing, if the determination amount is equal to or greater than the threshold value B, it is determined that the situation where the edging phenomenon occurs is found, while if the determination amount is less than the threshold value B, it is determined that the situation where the edging phenomenon occurs is not found.

According to the above processing, in the graph exemplifying changes over time in the determination amount in FIG. 33, since the determination amount at a time T0 is a value that is less than the threshold value B, it is determined that the situation where the edging phenomenon occurs is not found. Further, until a time T1, since the determination amount is a value that is less than the threshold value A, it is determined that the situation where the edging phenomenon occurs is not found.

On the other hand, when the time T1 is passed, since the determination amount is a value that is equal to or greater than the threshold value A, it is determined that the situation where the edging phenomenon occurs is found. Subsequently, although at the time point at which a time T2 is passed the determination amount becomes less than the threshold value A, at this time it is not determined that the situation where the edging phenomenon occurs is not found, and during a period until the determination amount becomes a value that is less than the threshold value B at a time T3, it is determined that the situation where the edging phenomenon occurs is found.

Subsequently, it is determined that the situation where the edging phenomenon occurs is not found when the determination amount becomes less than the threshold value B after passing the time T3.

Thus, at a time when it has been determined that the situation where the edging phenomenon occurs is not found it becomes difficult for a determination to be made to the effect that the situation where the edging phenomenon occurs is found, and furthermore, at a time when it has been determined that the situation where the edging phenomenon occurs is found it becomes difficult for a determination to be made to the effect that the situation where the edging phenomenon occurs is not found.

Accordingly, unnecessary changes in the exposure time are not performed by the edging phenomenon mitigation processing.

Note that a case where the determination amount is a value that is greater than or equal to the threshold value B and less than the threshold value A may be taken as a complete dead zone in which neither of the edging phenomenon mitigation processing and the normal state transition processing is executed.

Next, as erroneous detection prevention processing of form (Z), erroneous detection prevention processing in a case where the edging phenomenon detection processing of form (1) or form (2) is adopted and the edging phenomenon mitigation processing of form (b) or form (c) is adopted.

The erroneous detection prevention processing of form (Z) prevents erroneous detection which occurs due to appropriate detection of a situation in which the edging phenomenon occurs not being possible in the edging phenomenon detection processing of form (1) or form (2) due to execution of the edging phenomenon mitigation processing of form (b) or form (c).

When the edging phenomenon mitigation processing of form (b) or form (c) was executed, similarly to the description with respect to the erroneous detection prevention processing of form (Y), even if the situation where droplets are being scattered is found, it is difficult to detect the occurrence of the edging phenomenon. In particular, in a case where the edging phenomenon mitigation processing of form (c) was executed, the edging phenomenon does not occur even if the situation where droplets are scattering is found.

Consequently, similarly to the phenomenon described above with respect to the erroneous detection prevention processing of form (Y), unnecessary changing of the exposure time of the image pickup element 58 and unnecessary changing of the driving method is performed.

On the other hand, it is common for feeding of a fluid for air/water feeding or the like or suction to be continuously performed during a certain time period after the start thereof.

Therefore, by executing the following processing, erroneous detection of the existence or non-existence of occurrence of the edging phenomenon as described above is prevented, and this is also suitable for preventing unnecessary changes in the exposure time.

In the determination processing in step S12 after execution of the edging phenomenon detection processing of form (1) or form (2) in step S10 of FIG. 10, if it was determined in the previous determination processing that the situation where the edging phenomenon occurs is not found and it was determined in the current determination processing that the situation where the edging phenomenon occurs is found, the CPU 82 resets a timer and starts to measure the time.

Based on a time measurement value of the timer, during a period until a certain time period elapses after measurement of the time starts, the CPU 82 repeatedly executes the edging phenomenon mitigation processing in step S14 and does not execute the edging phenomenon detection processing in step S10. Note that in a case where the edging phenomenon mitigation processing of form (c) is adopted, this means driving of the image pickup element 58 by the pseudo-global shutter method is maintained.

In contrast, based on the time measurement value of the timer, when the certain time period has elapsed measurement of the time starts, the CPU 82 executes the normal state transition processing in step S16. Thereafter, the CPU 82 resumes the processing from the edging phenomenon detection processing in step S10.

Therefore, for a certain time period from when it is detected that the situation where the edging phenomenon occurs is found, edging phenomenon mitigation processing for a case in which the edging phenomenon has occurred is continuously performed, and when the certain time period elapses the edging phenomenon mitigation processing stops and processing is performed to return to the state at a time of normal imaging.

Accordingly, unnecessary changes to the exposure time of the image pickup element 58 and unnecessary changes to the driving method are not performed. Further, a time period in which feeding of a fluid for air/water feeding or the like from the air/water feeding nozzle 43 or suction is continuously performed can be known experientially, and by taking that time period into consideration when setting a value of the aforementioned certain time period, the operational state can be returned to the state at a time of normal imaging at a proper timing.

Although the endoscope apparatus and the image pickup control method thereof of the present invention have been described in detail above, it should be understood that the present invention is not limited to the above examples. Naturally, various improvements and modifications may be made within a range that does not depart from the spirit and scope of the present invention.

<Supplementary Notes>

As will be understood from the foregoing detailed description of the embodiments, the present specification includes disclosures of various technical concepts including the inventions described hereunder.

(Invention 1): An endoscope apparatus including: an image pickup device in which a plurality of pixels are arranged in a matrix shape, and which starts sequential exposure by at least one of scan lines with respect to the plurality of pixels to generate image data, and outputs image data for each of the scan lines in an order of starting exposure; a detection device that detects whether or not an image region at which a part of an object region is edged along a direction parallel to the scan lines in a state that is different to a case where a plurality of the scan lines are simultaneously exposed exists in a frame image due to differences of exposure timings for each of the scan lines of the image pickup device based on an image feature amount in the frame image that is obtained from the image data for each of the scan lines that is outputted from the image pickup device; and an exposure control device that changes an exposure time of each of the scan lines by the image pickup device simultaneously for all of the scan lines if the detection device detects the image region.

(Invention 2): The endoscope apparatus of invention 1, further including: an edge position candidate detection device that detects edge position candidates within the frame image based on a pixel value change amount in a direction perpendicular to the scan lines in the frame image; and an edge position detection device that detects an edge position within the frame image based on positional relationship between a plurality of the edge position candidates that are detected by the edge position candidate detection device, wherein in a case where the edge position detection device detects the edge position, the detection device detects a region including at least the edge position as the image region.

(Invention 3): The endoscope apparatus of invention 2, further including: a differential image generation device that generates a differential image between the frame image and an adjacent frame image that is temporally adjacent to the frame image; and a differential image edge position determination device that determines whether or not the edge position exists in the differential image, wherein in a case where the differential image edge position determination device determines that the edge position does not exist in the differential image, the detection device does not detect the region including at least the edge position as the image region.

(Invention 4): The endoscope apparatus of invention 1, further including: a differential image generation device that generates a differential image between the frame image and an adjacent frame image that is temporally adjacent to the frame image; an edge position candidate detection device that detects edge position candidates within the differential image based on a pixel value change amount in a direction perpendicular to the scan lines in the differential image; and an edge position detection device that detects an edge position within the differential image based on positional relationship between a plurality of the edge position candidates that are detected by the edge position candidate detection device, wherein in a case where the edge position detection device detects the edge position, the detection device detects a region including at least the edge position as the image region.

(Invention 5): The endoscope apparatus of any one of inventions 1 to 4, further including a pattern matching determination device that extracts a candidate region for the image region in the frame image, and determines whether or not the candidate region exists in an adjacent frame image that is temporally adjacent to the frame image by pattern matching processing, wherein in a case where the pattern matching determination device determines that the candidate region does not exist in the adjacent frame image, the detection device detects the candidate region as the image region.

(Invention 6): The endoscope apparatus of any one of inventions 1 to 5, further including: an irradiation device that irradiates illuminating light towards an object; and a light amount determination device that determines whether or not a light amount of the illuminating light is within a predetermined range, wherein in a case where the light amount determination device determines that the light amount is not within the predetermined range, the detection device does not perform detection of the image region.

(Invention 7): The endoscope apparatus of any one of inventions 1 to 6, further including: a high luminance region extraction device that extracts a high luminance region having a luminance value that is greater than a predetermined luminance value from within the frame image; and a high luminance region determination device that determines whether or not the area of the high luminance region is equal to or greater than a predetermined area, wherein in a case where the high luminance region determination device determines that the area of the high luminance region is equal to or greater than the predetermined area, the detection device does not detect the high luminance region as the image region.

(Invention 8): The endoscope apparatus of any one of inventions 1 to 7, further including a zoom optical device in which a focal distance is variable, wherein the detection device changes a threshold value for detecting the image region in accordance with the focal distance.

(Invention 9): The endoscope apparatus of any one of inventions 1 to 8, further including an image region occurrence degree determination device that calculates an average value of degrees of occurrence of the image region in each frame image in an immediately preceding predetermined time period, and determines whether or not the average value is equal to or less than a predetermined threshold value, wherein in a case where the image region occurrence degree determination device determines that the average value is equal to or less than the predetermined threshold value, even if the image region is detected, the detection device determines that the image region is not detected.

(Invention 10): The endoscope apparatus of any one of inventions 1 to 9, wherein in a case where the image region is not detected in a previous frame image with respect to the frame image, the detection device performs detection of the image region if the image feature amount of the frame image is greater than a first threshold value, and in a case where the image region is detected in the previous frame image, the detection device performs detection of the image region if the image feature amount of the frame image is greater than a second threshold value that is smaller than the first threshold value.

(Invention 11): The endoscope apparatus of any one of inventions 1 to 10, wherein in a case where the detection device detects the image region, until a certain time period elapses, the exposure control device continues control that changes an exposure time of each of the scan lines by the image pickup device simultaneously for all of the scan lines in comparison to a case where the detection device does not detect the image region.

(Invention 12): An endoscope apparatus, including: an image pickup device in which a plurality of pixels are arranged in a matrix shape, and which starts sequential exposure by at least one of scan lines with respect to the plurality of pixels to generate image data, and outputs image data for each of the scan lines in an order of starting exposure; a fluid operation detection device that detects a fluid operation that performs feeding or suction of a fluid to or from inside of a body; and an exposure control device that changes an exposure time of each of the scan lines by the image pickup device simultaneously for all of the scan lines if the fluid operation detection device detects the fluid operation.

(Invention 13): An image pickup control method of an endoscope apparatus, including: a step of starting sequential exposure by at least one of scan lines with respect to a plurality of pixels that are arranged in a matrix shape to generate image data, and outputting image data for each of the scan lines in an order of starting exposure; a step of detecting whether or not an image region at which a part of an object region is edged along a direction parallel to the scan lines in a state that is different to a case where a plurality of the scan lines are simultaneously exposed exists in a frame image due to differences of exposure timings for each of the scan lines based on an image feature amount in the frame image that is obtained from the image data for each of the scan lines; and a step of changing an exposure time of each of the scan lines simultaneously for all of the scan lines if the image region is detected.

(Invention 14): An image pickup control method of an endoscope apparatus, including: a step of starting sequential exposure by at least one of scan lines with respect to a plurality of pixels that are arranged in a matrix shape to generate image data, and outputting image data for each of the scan lines in an order of starting exposure; a step of detecting a fluid operation that performs feeding or suction of a fluid to or from inside of a body; and a step of changing an exposure time of each of the scan lines simultaneously for all of the scan lines if the fluid operation is detected.

What is claimed is:

1. An endoscope apparatus, comprising:
    an image pickup device in which a plurality of pixel sensors are arranged in a matrix shape, and which starts sequential exposure by at least one of pixel rows with respect to the plurality of pixel sensors to generate image data of a frame image, and outputs image data for each of the pixel rows in an order of starting exposure, wherein said pixel rows are made up of some of the plurality of pixel sensors;
    a detection device that determines if an image region exists in the frame image, the detection device determining a portion of the frame image to be the image region if said portion of the frame image includes a part of an object region that is edged along a direction parallel to the pixel rows in the frame image,
    wherein the image region is captured in the frame image by the image pickup device operating in a rolling shutter method, and
    wherein a first pixel row in the frame image in which an object that is moving at high speed appears and a second pixel row in the frame image in which the object that is moving at high speed does not appear arises since light reflected from the object that is moving at high speed appears only in a short time period, and wherein a boundary portion between the first and second pixel rows in the frame image in the direction parallel to the pixel rows is the edge of object region; and
    an exposure control device that, if the detection device determines the image region exists, changes an exposure time of each of the pixel rows by the image pickup device simultaneously for all of the pixel rows by the image pickup device if the detection device determines the image region exists, and does not change an entire exposure time of each of the pixel rows by the image pickup device simultaneously for all of the pixel rows by the image pickup device if the detection device does not determine the image region exists.

2. The endoscope apparatus according to claim 1, further comprising:
    an edge position candidate detection device that detects edge position candidates within the frame image based on a pixel value change amount in a direction perpendicular to the pixel rows in the frame image; and
    an edge position detection device that detects an edge position within the frame image based on positional relationship between a plurality of the edge position candidates that are detected by the edge position candidate detection device;
    wherein in a case where the edge position detection device determines the edge position, the detection device determines a portion of the frame image including at least the edge position as the image region.

3. The endoscope apparatus according to claim 2, further comprising:
    a differential image generation device that generates a differential image between the frame image and an adjacent frame image that is temporally adjacent to the frame image; and
    a differential image edge position determination device that determines whether or not the edge position exists in the differential image;
    wherein in a case where the differential image edge position determination device determines that the edge position does not exist in the differential image, the detection device does not determine the portion including at least the edge position as the image region.

4. The endoscope apparatus according to claim 1, further comprising:
    a differential image generation device that generates a differential image between the frame image and an adjacent frame image that is temporally adjacent to the frame image;
    an edge position candidate detection device that detects edge position candidates within the differential image based on a pixel value change amount in a direction perpendicular to the pixel rows in the differential image; and
    an edge position detection device that detects an edge position within the differential image based on positional relationship between a plurality of the edge position candidates that are detected by the edge position candidate detection device;
    wherein in a case where the edge position detection device determines the edge position, the detection device determines a portion of the frame image including at least the edge position as the image region.

5. The endoscope apparatus according to claim 1, further comprising:
a pattern matching determination device that extracts a candidate region for the image region in the frame image, and determines whether or not the candidate region exists in an adjacent frame image that is temporally adjacent to the frame image by pattern matching processing;
wherein in a case where the pattern matching determination device determines that the candidate region does not exist in the adjacent frame image, the detection device determines the candidate region as the image region.

6. The endoscope apparatus according to claim 1, further comprising:
an irradiation device that irradiates illuminating light towards an object; and
a light amount determination device that determines whether or not a light amount of the illuminating light is within a predetermined range;
wherein in a case where the light amount determination device determines that the light amount is not within the predetermined range, the detection device does not perform determination of the image region.

7. The endoscope apparatus according to claim 1, further comprising:
a high luminance region extraction device that extracts a high luminance region having a luminance value that is greater than a predetermined luminance value from within the frame image; and
a high luminance region determination device that determines whether or not the area of the high luminance region is equal to or greater than a predetermined area;
wherein in a case where the high luminance region determination device determines that the area of the high luminance region is equal to or greater than the predetermined area, the detection device does not determine the high luminance region as the image region.

8. The endoscope apparatus according to claim 1, further comprising:
a zoom optical device in which a focal distance is variable;
wherein the detection device changes a threshold value of a difference in pixel values between the first and second pixel rows for determining the edge of the object region for detecting the image region in accordance with the focal distance.

9. The endoscope apparatus according to claim 1, further comprising:
an image region occurrence degree determination device that calculates an average value of degrees of occurrence of the image region in each frame image in an immediately preceding predetermined time period, and determines whether or not the average value is equal to or less than a predetermined threshold value;
wherein in a case where the image region occurrence degree determination device determines that the average value is equal to or less than the predetermined threshold value, the detection device determines that the image region is not detected.

10. The endoscope apparatus according to claim 1, wherein in a case where the image region is not detected in a previous frame image with respect to the frame image, the detection device performs detection of the image region if a image feature amount of the frame image is greater than a first threshold value, and in a case where the image region is detected in the previous frame image, the detection device performs detection of the image region if the image feature amount of the frame image is greater than a second threshold value that is smaller than the first threshold value,
wherein the image feature amount is a number of horizontally clustered pixels detected in the image region or a number of candidate regions in the frame image, each of the candidate regions having an edge position.

11. The endoscope apparatus according to claim 1, wherein in a case where the detection device determines the image region, until a certain time period elapses, the exposure control device continues control that changes an entire exposure time of each of the pixel rows by the image pickup device simultaneously for all of the pixel rows by the image pickup device in comparison to a case where the detection device does not determine the image region.

* * * * *